United States Patent
Zhao et al.

(10) Patent No.: US 10,328,060 B2
(45) Date of Patent: Jun. 25, 2019

(54) CERTAIN PROTEIN KINASE INHIBITORS

(71) Applicants: Shanghai Fochon Pharmaceutical Co., Ltd., Shanghai (CN); Shanghai Institute of Materia Medica Chinese Academy of Sciences, Shanghai (CN); Chongqing Fochon Pharmaceutical Co., Ltd., Chongqing (CN)

(72) Inventors: Xingdong Zhao, Chongqing (CN); Jian Ding, Shanghai (CN); Linghua Meng, Shanghai (CN); Meiyu Geng, Shanghai (CN); Tongshuang Li, Surrey (CA); Zuwen Zhou, Chongqing (CN); Ling Chen, Chongqing (CN); Qihong Liu, Chongqing (CN); Xianlong Wang, Chongqing (CN); Lijun Yang, Chongqing (CN); Yue Rong, Chongqing (CN); Rui Tan, Chongqing (CN); Chuiliang Yu, Chongqing (CN); Lihua Jiang, Chongqing (CN); Yanxin Liu, Chongqing (CN); Li Linghu, Chongqing (CN); Jing Sun, Chongqing (CN); Weibo Wang, Moraga, CA (US)

(73) Assignees: SHANGHAI FOCHON PHARMACEUTICAL CO., LTD., Shanghai (CN); SHANGHAI INSTITUTE OF MATERIA MEDICA CHINESE ACADEMY OF SCIENCES, Shanghai (CN); CHONGQING FOCHON PHARMACEUTICAL CO., LTD., Chongqing (CN)

( * ) Notice: Subject to any disclaimer, the term of this patent is extended or adjusted under 35 U.S.C. 154(b) by 0 days.

(21) Appl. No.: 15/523,315

(22) PCT Filed: Nov. 1, 2015

(86) PCT No.: PCT/CN2015/093551
§ 371 (c)(1),
(2) Date: Apr. 28, 2017

(87) PCT Pub. No.: WO2016/066142
PCT Pub. Date: May 6, 2016

(65) Prior Publication Data
US 2018/0036293 A1 Feb. 8, 2018

Related U.S. Application Data

(60) Provisional application No. 62/073,993, filed on Nov. 1, 2014.

(51) Int. Cl.
| | |
|---|---|
| *C07D 519/00* | (2006.01) |
| *A61K 31/437* | (2006.01) |
| *A61K 45/06* | (2006.01) |
| *A61K 31/4375* | (2006.01) |
| *A61K 31/505* | (2006.01) |
| *A61K 31/52* | (2006.01) |

(52) U.S. Cl.
CPC ........ *A61K 31/437* (2013.01); *A61K 31/4375* (2013.01); *A61K 31/505* (2013.01); *A61K 31/52* (2013.01); *A61K 45/06* (2013.01); *C07D 519/00* (2013.01)

(58) Field of Classification Search
CPC .................................................... C07D 519/00
See application file for complete search history.

(56) References Cited

U.S. PATENT DOCUMENTS

2011/0015212 A1* 1/2011 Li ................. C07D 471/04
514/259.2

FOREIGN PATENT DOCUMENTS

| WO | WO-2005/113556 A1 | 12/2005 | |
|---|---|---|---|
| WO | WO-2008/064018 A1 | 5/2008 | |
| WO | WO-2011/008487 A1 | 1/2011 | |
| WO | WO-2012/146666 A1 | 11/2012 | |
| WO | WO-2016001855 A1 * | 1/2016 | ........... C07D 471/04 |

OTHER PUBLICATIONS

Wermuth, Camille G. "Molecular Variation Based on Isosteric Replacements" in Chapter 13, The Practice of Medicinal Chemistry, Academic: 1996, pp. 203-237.*
International Search Report for PCT/CN2015/093551 dated Feb. 3, 2016.
Written Opinion for PCT/CN2015/093551 dated Feb. 3, 2016.
J.A. Joule and K. Mills, "The Diazines: Pyridazine, Pyrimidine, and Pyrazine: Reactions and Synthesis", Heterocyclic Chemistry, 5$^{th}$ Ed., p. 253-254 (2010).
European Supplementary Search Report, issued in European Patent Application No. 15855878.3, 7 pages (dated Jul. 11, 2018).
Wermuth, "Classic Bioisostere Atoms and Groups", The Practice of Medicinal Chemistry, 3rd Ed., p. 294 (Table 15.4) (2008).

* cited by examiner

*Primary Examiner* — David K O'Dell
(74) *Attorney, Agent, or Firm* — Foley & Lardner LLP

(57) ABSTRACT

Provided are certain PI3K inhibitors, pharmaceutical compositions thereof, and methods of use therefor.

15 Claims, No Drawings

CERTAIN PROTEIN KINASE INHIBITORS

CROSS REFERENCE TO RELATED APPLICATIONS

The present application is a national stage application, filed under 35 U.S.C. § 371, of PCT Application No. PCT/CN2015/093551, filed Nov. 1, 2015 entitled "CERTAIN PROTEIN KINASE INHIBITORS," which claims priority to U.S. Provisional Patent Application 62/073,993, filed Nov. 1, 2014, all of which are hereby incorporated by reference in their entireties.

TECHNICAL FIELD

Provided are certain compounds and/or pharmaceutically acceptable salts thereof which can inhibit kinase activity of PI3K and may be useful for the treatment of hyper-proliferative diseases like inflammatory and autoimmune disorders and cancer.

BACKGROUND

Phosphoinositide 3-kinase (PI3K) belongs to a large family of lipid signaling kinase that plays key role in cellular processes, including cell growth, differentiation, migration and apoptosis. PI3K family is divided to three classes, I, II and III, based on sequence homology and lipid substrate specificity. Among them, Class I PI3K, which includes PI3Kα, PI3Kβ, PI3Kγ, and PI3Kδ, is most studied.

Class I PI3K is a heterodimer formed by two subunits, a catalytic subunit (p110) and a regulatory subunit (p85). The catalytic subunit, p110, has four isotypes, α, β, γ, and δ. The p110α has a role in insulin-dependent signaling, p110β in platelet aggregation, thrombosis and insulin signaling, and p110γ and p110δ are expressed mainly in leukocytes and have roles in lymphocyte activation, mast cell degranulation, and chemotaxis. The catalytic p110 subunit associates with p85 regulatory subunit. Upon reception of upstream activation signals, the p85 regulatory subunit releases its inhibition of p110, such that p110 can interact with the lipid membranes to phosphorylate phosphatidylinositol-4,5-bisphosphate (PIP2) at the 3'-OH position of the inositol ring to generate phosphatidylinositol-3,4,5-trisphosphate (PIP3), which then activates downstream signals, resulting in dysregulation of metabolism and protein synthesis, and cell growth, proliferation and survival.

All four class I catalytic PI3K isoforms show a characteristic expression pattern in vivo. p110α and p110β are expressed ubiquitously in mammalian tissue, while p110γ and p110δ appear to be more selectively expressed in leukocyte, endothelial cells and smooth muscle cells. Deletion of the p110α or p110β induces embryonic lethality. p110γ-deficient mice develop and reproduce normally, although they have suboptimal immune responses because of defects in T-cell activation as well as in neutrophil and macrophage migration. The loss of p110δ mice are also viable and fertile but exhibit significant defects in T, B cell activation.

The PI3K pathway is commonly deregulated in cancer cells. The expression of PI3Kδ is generally restricted to hematopoietic cell types. The p110δ isoform is constitutively activated in B cell tumors, and inactivation of it have demonstrated its important role for treatment of B cell malignancy. It's demonstrated that the PI3Kδ plays a critical role in the signaling pathways of various types of leukemia. Hence, it has become an attractive target for pharmacotherapy. Preclinical data on acute myeloid leukemia and chronic lymphocytic leukemia has identified the PI3Kδ as predominant isoform in these diseases. Therefore, a compound having an inhibitory activity on PI3K will be useful for the prevention and treatment of cancer.

In addition to cancer, PI3K has also been suggested as a target for inflammatory and autoimmune disorders.

Although PI3K inhibitors were disclosed in the arts, e.g. WO 2012146666, WO 2003035075 and US 20110015212, many suffer from short half-life or toxicity. Therefore, there is a need for new PI3K inhibitors that have at least one advantageous property selected from potency, stability, selectivity, toxicity and pharmacodynamics properties as an alternative for the treatment of hyper-proliferative diseases. In this regard, a novel class of PI3K inhibitors is provided herein.

DISCLOSURE OF THE INVENTION

Disclosed herein are certain novel 6-6 or 6-5 membered fused pyridone ring derivatives and pharmaceutical compositions thereof, and their use as pharmaceuticals.

In one aspect, disclosed herein is a compound of formula (I):

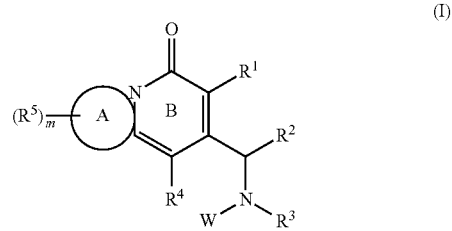

and/or a pharmaceutically acceptable salt thereof,
wherein:
A-B is a 6-6 or 5-6 membered fused pyridone ring system, preferably is selected from:

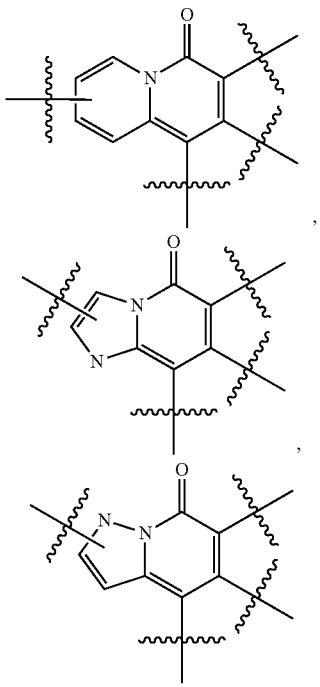

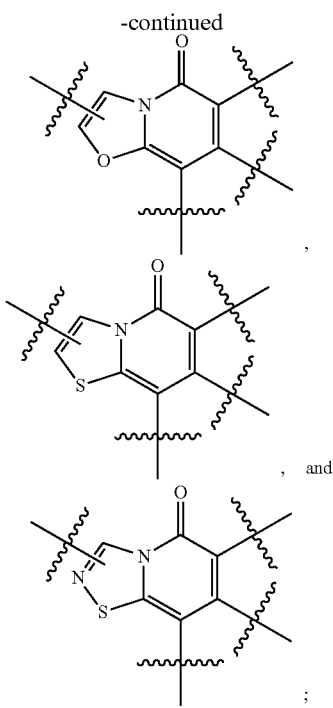

W is selected from aryl and heteroaryl, wherein aryl and heteroaryl are each unsubstituted or substituted with at least one substituent, such as one, two, three, or four substituents, independently selected from $R^{6b}$;

$R^1$ is selected from hydrogen, halogen, cyano, $C_{1-10}$ alkyl (such as $C_{1-6}$ alkyl), $C_{2-10}$ alkenyl, $C_{2-10}$ alkynyl, $C_{3-10}$ cycloalkyl (such as $C_{3-6}$ cycloalkyl), $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;

$R^2$ is selected from hydrogen, $C_{1-10}$ alkyl (such as $C_{1-6}$ alkyl), $C_{2-10}$ alkenyl, $C_{2-10}$ alkynyl, $C_{3-10}$ cycloalkyl (such as $C_{3-6}$ cycloalkyl), $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

$R^3$ is selected from hydrogen, $C_{1-10}$ alkyl, and $C_{3-10}$ cycloalkyl, wherein alkyl and cycloalkyl are each unsubstituted or substituted with at least one substituent, such as one, two, three, or four substituents, independently selected from $R^{6a}$;

$R^4$ is selected from hydrogen, halogen, cyano, $C_{1-10}$ alkyl, $C_{2-10}$ alkenyl, $C_{2-10}$ alkynyl, $C_{3-10}$ cycloalkyl, and $C_{3-10}$ cycloalkyl-$C_{1-4}$ alkyl, wherein alkyl, alkenyl, alkynyl, and cycloalkyl are each unsubstituted or substituted with at least one substituent, such as one, two, three, or four substituents, independently selected from $R^{6a}$;

each $R^5$ is independently selected from hydrogen, $C_{1-10}$ alkyl (such as $C_{1-6}$ alkyl), $C_{2-10}$ alkenyl, $C_{2-10}$ alkynyl, $C_{3-10}$ cycloalkyl, $C_{3-10}$ cycloalkyl-$C_{1-4}$ alkyl, $OR^8$, $NR^7S(O)_rR^8$, $NO_2$, halogen, $S(O)_rR^7$, $SR^8$, $S(O)_2OR^7$, $OS(O)_2R^8$, $S(O)_r$ $NR^7R^8$, $NR^7R^8$, $O(CR^9R^{10})_rNR^7R^8$, $C(O)R^7$, $CO_2R^8$, $CO_2$ $(CR^9R^{10})_rCONR^7R^8$, $OC(O)R^7$, $CN$, $C(O)NR^7R^8$, $NR^7C$ $(O)R^8$, $OC(O)NR^7R^8$, $NR^7C(O)OR^8$, $NR^7C(O)NR^7R^8$, $CR^7$ $(N-OR^8)$, $CHF_2$, $CF_3$, $OCHF_2$, and $OCF_3$, wherein alkyl, alkenyl, alkynyl, and cycloalkyl are each unsubstituted or substituted with at least one substituent, such as one, two, three, or four substituents, independently selected from $R^{6a}$;

each $R^{6a}$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $OR^8$, $NR^7S(O)_rR^8$, $NO_2$, halogen, $S(O)_rR^7$, $SR^8$, $S(O)_2OR^7$, $OS(O)_2R^8$, $S(O)_rNR^7R^8$, $NR^7R^8$, $(CR^9R^{10})_t$ $OR^8$, $(CR^9R^{10})_tNR^7R^8$, $(CR^9R^{10})_tSR^8$, $(CR^9R^{10})_tS(O)_rR^8$, $(CR^9R^{10})_tCO_2R^8$, $(CR^9R^{10})_tCONR^7R^8$, $(CR^9R^{10})_t$ $NR^7CO_2R^8$, $(CR^9R^{10})_tOCONR^7R^8$, $(CR^9R^{10})_t$ $NR^7CONR^7R^8$, $(CR^9R^{10})_tNR^7SO_2NR^7R^8$, $O(CR^9R^{10})_t$ $NR^7R^8$, $C(O)R^7$, $C(O)(CR^9R^{10})_tOR^8$, $C(O)(CR^9R^{10})_t$ $NR^7R^8$, $C(O)(CR^9R^{10})_tSR^8$, $C(O)(CR^9R^{10})_tS(O)_rR^8$, $CO_2R^8$, $CO_2(CR^9R^{10})_tCONR^7R^8$, $OC(O)R^7$, $CN$, $C(O)$ $NR^7R^8$, $NR^7C(O)R^8$, $OC(O)NR^7R^8$, $NR^7C(O)OR^8$, $NR^7C$ $(O)NR^7R^8$, $CR^7(N-OR^8)$, $CHF_2$, $CF_3$, $OCHF_2$, and $OCF_3$;

each $R^{6b}$ is independently selected from $R^{6a}$, aryl, aryl-$C_{1-4}$ alkyl, heteroaryl, and heteroaryl-$C_{1-4}$ alkyl;

each $R^7$ and each $R^8$ are independently selected from: hydrogen, $C_{1-10}$ alkyl, $C_{2-10}$ alkenyl, $C_{2-10}$ alkynyl, cycloalkyl, cycloalkyl-$C_{1-4}$ alkyl; heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and aryl and heteroaryl are each unsubstituted or substituted with at least one substituent, such as one, two, three, or four substituents, independently selected from $R^{6b}$; or, $R^7$ and $R^8$ together with the atom(s) to which they are attached form a heterocyclic ring of 4 to 12 members containing 0, 1, or 2 additional heteroatoms independently selected from oxygen, sulfur and nitrogen, and optionally substituted with for 2 $R^{6b}$ groups;

each $R^9$ and each $R^{10}$ are independently selected from hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; or, $R^9$ and $R^{10}$ together with the carbon atom(s) to which they are attached form a ring of 3 to 7 members containing 0, 1, or 2 heteroatoms independently selected from oxygen, sulfur and nitrogen, and optionally substituted with for 2 $R^{6a}$ groups;

m is independently selected from 0, 1, 2, 3 and 4;
each r is independently selected from 1 and 2;
each t is independently selected from 1, 2, and 3.

In another aspect, disclosed is a pharmaceutical composition comprising a compound of formula (I) and/or a pharmaceutically acceptable salt thereof and a pharmaceutically acceptable excipient.

In yet another aspect, disclosed is a method for modulating PI3K, comprising administering to a system or a subject in need thereof, a therapeutically effective amount of a compound of formula (I) and/or a pharmaceutically acceptable salt thereof or a pharmaceutical composition thereof.

In yet another aspect, disclosed is a method to treat, ameliorate or prevent a condition which responds to inhibition of PI3K comprising administering to a system or subject in need of such treatment an effective amount of a compound of formula (I) and/or a pharmaceutically acceptable salt thereof or a pharmaceutical composition thereof, and optionally in combination with a second therapeutic agent, thereby treating said condition.

Alternatively, disclosed is the use of a compound of formula (I) and/or a pharmaceutically acceptable salt thereof in the manufacture of a medicament for treating a condition mediated by PI3K. In particular embodiments, the compounds of the disclosure may be used alone or in combination with a second therapeutic agent to treat a condition mediated by PI3K.

Alternatively, disclosed is a compound of formula (I) for treating a condition mediated by PI3K.

Specifically, the condition herein includes but not limited to, an autoimmune disease, a transplantation disease, an infectious disease or a cell proliferative disorder.

Furthermore, disclosed is a method for treating a cell proliferative disorder, comprising administering to a system or subject in need of such treatment an effective amount of a compound of formula (I) and/or a pharmaceutically acceptable salt thereof or a pharmaceutical composition thereof, and optionally in combination with a second therapeutic agent, thereby treating said condition.

Alternatively, disclosed is the use of a compound of formula (I) and/or a pharmaceutically acceptable salt thereof in the manufacture of a medicament for treating a cell-proliferative disorder. In particular examples, the compounds of the disclosure may be used alone or in combination with a chemotherapeutic agent to treat a cell proliferative disorder.

Specifically, the cell proliferative disorder disclosed herein includes but not limited to, lymphoma, osteosarcoma, melanoma, or a tumor of breast, renal, prostate, colorectal, thyroid, ovarian, pancreatic, neuronal, lung, uterine or gastrointestinal tumor.

In the above method(s) for using the compounds of the disclosure, a compound of formula (I) and/or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "alkyl" refers to both branched and straight-chain saturated aliphatic hydrocarbon groups having the specified number of carbon atoms. Unless otherwise specified, "alkyl" refers to $C_1$-$C_6$ alkyl. For example, $C_1$-$C_6$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl" means a saturated aliphatic cyclic hydrocarbon group having the specified number of carbon atoms. Unless otherwise specified, "cycloalkyl" refers to $C_{3-10}$ cycloalkyl. For example, "cycloalkyl" includes but is not limited to cyclopropyl, methyl-cyclopropyl, 2,2-dimethyl-cyclobutyl, 2-ethyl-cyclopentyl, and cyclohexyl.

The term "alkenyl" refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "aryl" encompasses: 5- and 6-membered carbocyclic aromatic rings, for example, benzene; bicyclic ring systems wherein at least one ring is carbocyclic and aromatic, for example, naphthalene, indane, and 1,2,3,4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl" refers to
- 5- to 8-membered aromatic, monocyclic rings containing one or more, for example, from 1 to 4, or, in some embodiments, from 1 to 3, heteroatoms selected from N, O, and S, with the remaining ring atoms being carbon;
- 8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and
- 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include, but are not limited to, pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

In the disclosure, the language of 6-6 or 5-6 membered fused ring system is used for representing two 6-membered aryl or heteroaryl are fused together or a 5-membered aryl or heteroaryl is fused with 6-membered aryl or heteroaryl. For example, a 6-6 or 5-6 membered fused pyridone ring system refers to a 6-membered aryl or heteroaryl is fused with pyridone ring, or a 5-membered aryl or heteroaryl fused with pyridone ring.

The term "heterocycle" (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, and nitrogen, as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, and nitrogen. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, but are not limited to (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl. Bicyclic heterocycles include, but are not limited to,

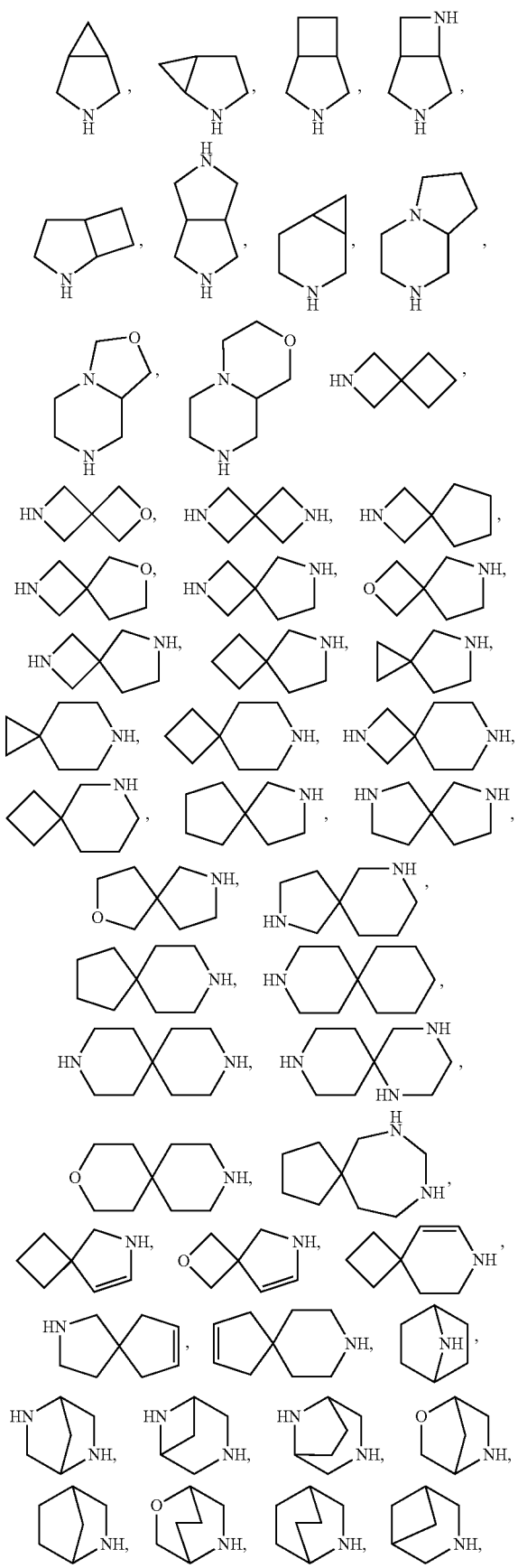

-continued

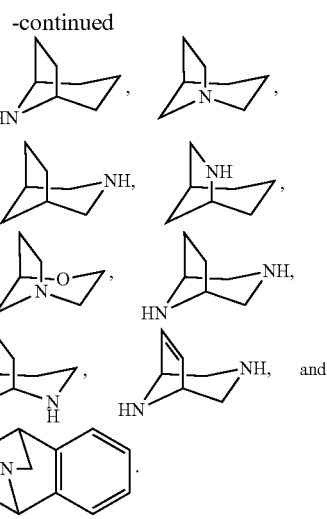

As used herein, "arylalkyl" refers to an alkyl moiety substituted by an aryl group. Example arylalkyl groups include benzyl, phenethyl, and naphthylmethyl groups. In some embodiments, arylalkyl groups have from 7 to 20 or 7 to 11 carbon atoms. When used in the phrase "aryl$C_{1-4}$ alkyl", the term "$C_{1-4}$" refers to the alkyl portion of the moiety and does not describe the number of atoms in the aryl portion of the moiety. Likewise, when used in the phrase "aryl$C_{1-10}$ alkyl", the term "$C_{1-10}$" refers to the alkyl portion of the moiety and does not describe the number of atoms in the aryl portion of the moiety.

As used herein, "heterocyclylalkyl" refers to alkyl substituted by heterocyclyl. When used in the phrase "heterocyclyl-$C_{1-6}$ alkyl", the term "$C_{1-6}$" refers to the alkyl portion of the moiety and does not describe the number of atoms in the heterocyclyl portion of the moiety.

As used herein, "cycloalkylalkyl" refers to alkyl substituted by cycloalkyl. When used in the phrase "$C_{3-10}$ cycloalkylalkyl", the term "$C_{3-10}$" refers to the cycloalkyl portion of the moiety and does not describe the number of atoms in the alkyl portion of the moiety. When used in the phrase "$C_{3-7}$ cycloalkylalkyl", the term "$C_{3-7}$" refers to the cycloalkyl portion of the moiety and does not describe the number of atoms in the alkyl portion of the moiety. When used in the phrase "$C_{3-8}$ cycloalkylalkyl", the term "$C_{3-8}$" refers to the cycloalkyl portion of the moiety and does not describe the number of atoms in the alkyl portion of the moiety. When used in the phrase "cycloalkyl $C_{1-10}$ alkyl", the term "$C_{1-10}$" refers to the alkyl portion of the moiety and does not describe the number of atoms in the cycloalkyl portion of the moiety.

As used herein, "heteroarylalkyl" refers to alkyl substituted by heteroaryl. When used in the phrase "heteroaryl $C_{1-4}$ alkyl", the term "$C_{1-4}$" refers to the alkyl portion of the moiety and does not describe the number of atoms in the heteroaryl portion of the moiety. Likewise, when used in the phrase "heteroaryl $C_{1-10}$ alkyl", the term "$C_{1-10}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is arylalkyl, the aryl portion may be unsubstituted or substituted with at least one substituent, such as one, two, three, or four substituents, independently selected from $R^{6b}$ and the alkyl portion may also be unsubstituted or substituted with at least one substituent, such as one, two, three, or four substituents, independently selected from $R^{6a}$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using a pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trim ethyl silyl)ethoxymethyl, 2-(p-toluenesulfonyl)ethyl, 2-(p-nitrophenyl sulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "administration of" and or "administering" a compound and/or a pharmaceutically acceptable salt should be understood to mean providing a compound and/or a pharmaceutically acceptable salt thereof to the individual in recognized need of treatment.

The term "effective amount" means the amount of the a compound and/or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

1. A compound of formula (I):

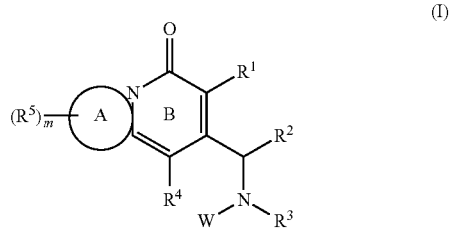

(I)

and/or a pharmaceutically acceptable salt thereof, wherein:

A-B is a 6-6 or 5-6 membered fused pyridone ring system, selected from:

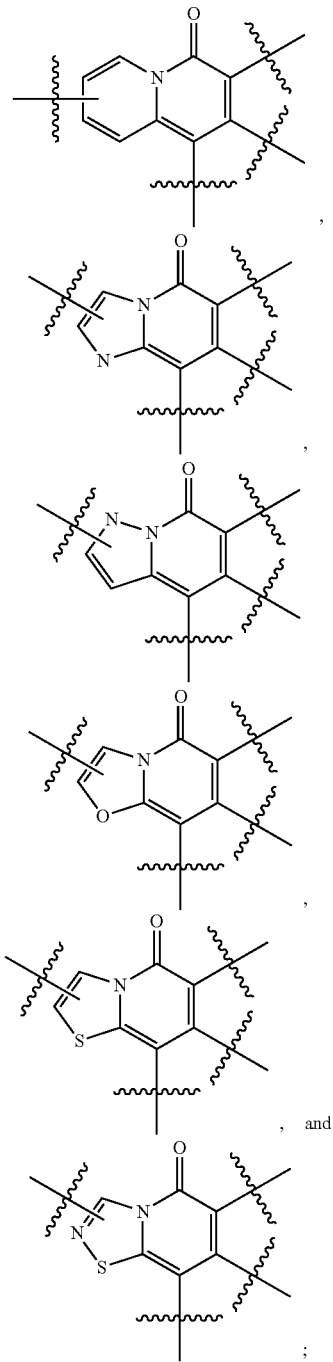

W is selected from aryl and heteroaryl, wherein aryl and heteroaryl are each unsubstituted or substituted with at least one substituent, such as one, two, three, or four substituents, independently selected from $R^{6b}$;

$R^1$ is selected from hydrogen, halogen, cyano, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or substituted with at least one substituent, such as one, two, three, or four substituents, independently selected from $R^{6b}$;

$R^2$ is selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

$R^3$ is selected from hydrogen, $C_{1-10}$ alkyl, and $C_{3-10}$ cycloalkyl, wherein alkyl and cycloalkyl are each unsubstituted or substituted with at least one substituent, such as one, two, three, or four substituents, independently selected from $R^{6a}$;

$R^4$ is selected from hydrogen, halogen, cyano, $C_{1-10}$ alkyl, $C_{2-10}$ alkenyl, $C_{2-10}$ alkynyl, $C_{3-10}$ cycloalkyl, and $C_{3-10}$ cycloalkyl-$C_{1-4}$ alkyl, wherein alkyl, alkenyl, alkynyl, and cycloalkyl are each unsubstituted or substituted with at least one substituent, such as one, two, three, or four substituents, independently selected from $R^{6a}$;

each $R^5$ is independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $OR^8$, $NR^7S(O)_tR^8$, $NO_2$, halogen, $S(O)_tR^7$, $SR^8$, $S(O)_2OR^7$, $OS(O)_2R^8$, $S(O)_tNR^7R^8$, $NR^7R^8$, $O(CR^9R^{10})_tNR^7R^8$, $C(O)R^7$, $CO_2R^8$, $CO_2(CR^9R^{10})_tCONR^7R^8$, $OC(O)R^7$, $CN$, $C(O)NR^7R^8$, $NR^7C(O)R^8$, $OC(O)NR^7R^8$, $NR^7C(O)OR^8$, $NR^7C(O)NR^7R^8$, $CR^7(N\!\!=\!\!OR^8)$, $CHF_2$, $CF_3$, $OCHF_2$, and $OCF_3$, wherein alkyl, alkenyl, alkynyl, and cycloalkyl are each unsubstituted or substituted with at least one substituent, such as one, two, three, or four substituents, independently selected from $R^{6a}$;

each $R^{6a}$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $OR^8$, $NR^7S(O)_tR^8$, $NO_2$, halogen, $S(O)_tR^7$, $SR^8$, $S(O)_2OR^7$, $OS(O)_2R^8$, $S(O)_tNR^7R^8$, $NR^7R^8$, $(CR^9R^{10})_tOR^8$, $(CR^9R^{10})_tNR^7R^8$, $(CR^9R^{10})_tSR^8$, $(CR^9R^{10})_tS(O)_tR^8$, $(CR^9R^{10})_tCO_2R^8$, $(CR^9R^{10})_tCONR^7R^8$, $(CR^9R^{10})_tNR^7CO_2R^8$, $(CR^9R^{10})_tOCONR^7R^8$, $(CR^9R^{10})_tNR^7CONR^7R^8$, $(CR^9R^{10})_tNR^7SO_2NR^7R^8$, $O(CR^9R^{10})_tNR^7R^8$, $C(O)R^7$, $C(O)(CR^9R^{10})_tOR^8$, $C(O)(CR^9R^{10})_tNR^7R^8$, $C(O)(CR^9R^{10})_tSR^8$, $C(O)(CR^9R^{10})_tS(O)_tR^8$, $CO_2R^8$, $CO_2(CR^9R^{10})_tCONR^7R^8$, $OC(O)R^7$, $CN$, $C(O)NR^7R^8$, $NR^7C(O)R^8$, $OC(O)NR^7R^8$, $NR^7C(O)OR^8$, $NR^7C(O)NR^7R^8$, $CR^7(N\!\!=\!\!OR^8)$, $CHF_2$, $CF_3$, $OCHF_2$, and $OCF_3$;

each $R^{6b}$ is independently selected from $R^{6a}$, aryl, aryl-$C_{1-4}$ alkyl, heterocyclyl, and heteroaryl-$C_{1-4}$ alkyl;

each $R^7$ and each $R^8$ are independently selected from hydrogen, $C_{1-10}$ alkyl, $C_{2-10}$ alkenyl, $C_{2-10}$ alkynyl, cycloalkyl, cycloalkyl-$C_{1-4}$ alkyl; heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, and heterocyclyl are each unsubstituted or substituted with at least one substituent, such as one, two, three, or four substituents, independently selected from $R^{6a}$, and aryl and heteroaryl are each unsubstituted or substituted with at least one substituent, such as one, two, three, or four substituents, independently selected from $R^{6b}$; or, $R^7$ and $R^8$ together with the atom(s) to which they are attached form a heterocyclic ring of 4 to 12 members containing 0, 1, or 2 additional heteroatoms independently selected from oxygen, sulfur and nitrogen, and optionally substituted with 1-2 $R^{6b}$ groups;

each $R^9$ and each $R^{10}$ are independently selected from hydrogen, $C_{1-10}$ alkyl, $C_{2-10}$ alkenyl, $C_{2-10}$ alkynyl, cycloalkyl, cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl; or, $R^9$ and $R^{10}$ together with the carbon atom(s) to which they are attached form a ring of 3 to 7 members containing 0, 1, or 2 heteroatoms independently selected from oxygen, sulfur and nitrogen, and optionally substituted with 1-2 $R^{6a}$ groups;

m is independently selected from 0, 1, 2, 3 and 4;
each r is independently selected from 1 and 2;
each t is independently selected from 1, 2, and 3.

2. A compound of 1 and/or a pharmaceutically acceptable salt thereof, wherein A-B is selected from

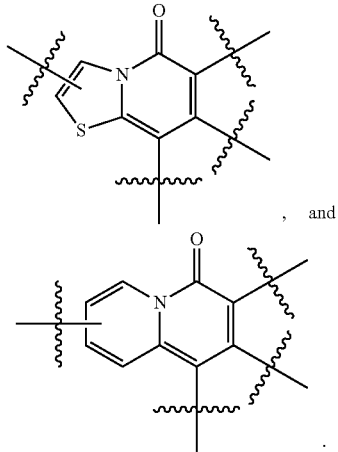

, and

3. A compound of 2 and/or a pharmaceutically acceptable salt thereof, wherein A-B is

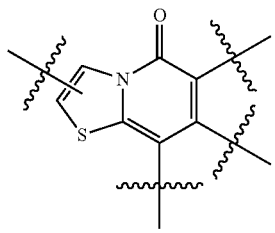

4. A compound of 3 and/or a pharmaceutically acceptable salt thereof, wherein A-B is

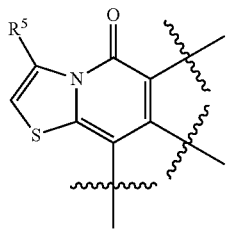

5. A compound of any one of 1 to 4 and/or a pharmaceutically acceptable salt thereof, wherein $R^5$ is selected from hydrogen, halogen, $CF_3$, $C_{1-10}$ alkyl, and $C_{3-10}$ cycloalkyl, wherein alkyl and cycloalkyl are each unsubstituted or substituted with at least one substituent, such as one, two, three, or four substituents, independently selected from $R^{6a}$, $R^{6a}$ is described as in 1.

6. A compound of 5 and/or a pharmaceutically acceptable salt thereof, wherein $R^5$ is selected from hydrogen, halogen, methyl, ethyl, $CF_3$, and cyclopropyl.

7. A compound of 6 and/or a pharmaceutically acceptable salt thereof, wherein $R^5$ is selected from hydrogen, chloro, methyl, ethyl, $CF_3$, and cyclopropyl.

8. A compound of 7 and/or a pharmaceutically acceptable salt thereof, wherein $R^5$ is selected from chloro, methyl and $CF_3$.

9. A compound of any one of 1 to 8 and/or a pharmaceutically acceptable salt thereof, wherein $R^1$ is aryl, wherein aryl is unsubstituted or substituted with at least one substituent, such as one, two, three, or four substituents, independently selected from $R^{6b}$, $R^{6b}$ is described as in 1.

10. A compound of 9 and/or a pharmaceutically acceptable salt thereof, wherein $R^1$ is phenyl, which is unsubstituted or substituted with at least one substituent, such as one, two, three, or four substituents, independently selected from $R^{6b}$, preferably $R^{6b}$ is halogen.

11. A compound of 10 and/or a pharmaceutically acceptable salt thereof, wherein $R^1$ is phenyl, which is unsubstituted or substituted with fluoro.

12. A compound of any one of 1 to 11 and/or a pharmaceutically acceptable salt thereof, wherein $R^2$ is selected from $C_{1-10}$ alkyl and $C_{3-10}$ cycloalkyl, wherein alkyl and cycloalkyl are unsubstituted or substituted with at least one substituent, such as one, two, three, or four substituents, independently selected from $R^{6a}$, $R^{6a}$ is described as in 1.

13. A compound of 12 and/or a pharmaceutically acceptable salt thereof, wherein $R^2$ is selected from methyl, ethyl, isopropyl and cyclopropyl.

14. A compound of any one of 1 to 13 and/or a pharmaceutically acceptable salt thereof, wherein W is heteroaryl, wherein heteroaryl is unsubstituted or substituted with at least one substituent, such as one, two, three, or four substituents, independently selected from $R^{6b}$.

15. A compound of 14 and/or a pharmaceutically acceptable salt thereof, wherein W is

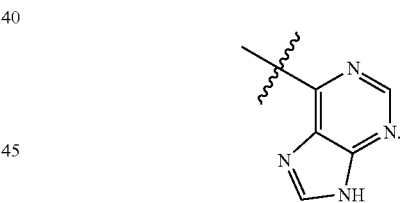

16. A compound of 14 and/or a pharmaceutically acceptable salt thereof, wherein W is pyrimidine, wherein pyrimidine is unsubstituted or substituted with at least one substituent, such as one, two, three, or four substituents, independently selected from $R^{6b}$, $R^{6b}$ is described as in 1.

17. A compound of 16 and/or a pharmaceutically acceptable salt thereof, wherein W is

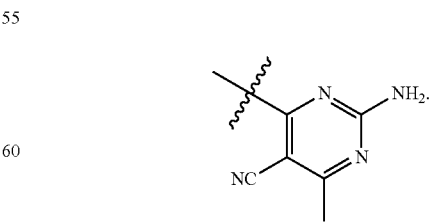

18. A compound of any one of 1 to 17 and/or a pharmaceutically acceptable salt thereof, wherein $R^3$ is hydrogen.

19. A compound of any one of 1 to 18 and/or a pharmaceutically acceptable salt thereof, wherein $R^4$ is hydrogen.

20. A compound, selected from
7-(1-((9H-purin-6-yl)amino)ethyl)-3-methyl-6-phenyl-5H-thiazolo[3,2-a]pyridin-5-one,
7-(1-((9H-purin-6-yl)amino)propyl)-3-methyl-6-phenyl-5H-thiazolo[3,2-a]pyridin-5-one,
2-(1-((9H-purin-6-yl)amino)ethyl)-3-phenyl-4H-quinolizin-4-one,
2-(1-((9H-purin-6-yl)amino)propyl)-3-phenyl-4H-quinolizin-4-one,
7-(1-((9H-purin-6-yl)amino)ethyl)-6-(4-fluorophenyl)-3-methyl-5H-thiazolo[3,2-a]pyridin-5-one,
7-(1-((9H-purin-6-yl)amino)propyl)-6-(4-fluorophenyl)-3-methyl-5H-thiazolo[3,2-a]pyridin-5-one,
7-(1-((9H-purin-6-yl)amino)ethyl)-6-(2-fluorophenyl)-3-methyl-5H-thiazolo[3,2-a]pyridin-5-one,
7-(1-((9H-purin-6-yl)amino)ethyl)-6-(3-fluorophenyl)-3-methyl-5H-thiazolo[3,2-a]pyridin-5-one,
7-(1-((9H-purin-6-yl)amino)ethyl)-3-ethyl-6-phenyl-5H-thiazolo[3,2-a]pyridin-5-one,
7-(1-((9H-purin-6-yl)amino)propyl)-6-(2-fluorophenyl)-3-methyl-5H-thiazolo[3,2-a]pyridin-5-one,
7-(1-((9H-purin-6-yl)amino)propyl)-6-(3-fluorophenyl)-3-methyl-5H-thiazolo[3,2-a]pyridin-5-one,
7-(1-((9H-purin-6-yl)amino)ethyl)-3-chloro-6-(3-fluorophenyl)-5H-thiazolo[3,2-a]pyridin-5-one,
7-(1-((9H-purin-6-yl)amino)propyl)-3-chloro-6-(3-fluorophenyl)-5H-thiazol o[3,2-a]pyridin-5-one,
7-(1-((9H-purin-6-yl)amino)ethyl)-3-chloro-6-phenyl-5H-thiazolo[3,2-a]pyridin-5-one,
7-(1-((9H-purin-6-yl)amino)propyl)-3-chloro-6-phenyl-5H-thiazolo[3,2-a]pyridin-5-one,
7-(1-((9H-purin-6-yl)amino)ethyl)-6-(3-fluorophenyl)-3-(trifluoromethyl)-5H-thiazolo[3,2-a]pyridin-5-one,
7-(1-((9H-purin-6-yl)amino)propyl)-6-(3-fluorophenyl)-3-(trifluoromethyl)-5H-thiazolo[3,2-a]pyridin-5-one,
7-(1-((9H-purin-6-yl)amino)ethyl)-6-phenyl-3-(trifluoromethyl)-5H-thiazolo[3,2-a]pyridin-5-one,
7-(1-((9H-purin-6-yl)amino)propyl)-6-phenyl-3-(trifluoromethyl)-5H-thiazolo[3,2-a]pyridin-5-one,
7-(((9H-purin-6-yl)amino)(cyclopropyl)methyl)-3-chloro-6-(3-fluorophenyl)-5H-thiazolo[3,2-a]pyridin-5-one,
7-(((9H-purin-6-yl)amino)(cyclopropyl)methyl)-3-chloro-6-phenyl-5H-thiazolo[3,2-a]pyridin-5-one,
7-(((9H-purin-6-yl)amino)(cyclopropyl)methyl)-6-(3-fluorophenyl)-3-(trifluoromethyl)-5H-thiazolo[3,2-a]pyridin-5-one,
7-(((9H-purin-6-yl)amino)(cyclopropyl)methyl)-6-phenyl-3-(trifluoromethyl)-5H-thiazolo[3,2-a]pyridin-5-one,
7-(((9H-purin-6-yl)amino)(cyclopropyl)methyl)-3-methyl-6-phenyl-5H-thiazolo[3,2-a]pyridin-5-one,
7-(((9H-purin-6-yl)amino)(cyclopropyl)methyl)-6-(3-fluorophenyl)-3-methyl-5H-thiazolo[3,2-a]pyridin-5-one
2-amino-4-methyl-6-((1-(3-methyl-5-oxo-6-phenyl-5H-thiazolo[3,2-a]pyridin-7-yl)ethyl)amino)pyrimidine-5-carbonitrile,
2-amino-4-((1-(3-chloro-6-(3-fluorophenyl)-5-oxo-5H-thiazolo[3,2-a]pyridin-7-yl)ethyl)amino)-6-methylpyrimidine-5-carbonitrile,
and/or pharmaceutically acceptable salt thereof.

In another of its aspects, provided is a pharmaceutical composition comprising a compound according to any one of 1-20, and/or a pharmaceutically acceptable salts thereof.

In yet another of its aspects, provided is a kit comprising a compound of any one of 1-20, and/or a pharmaceutically acceptable salts thereof and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of 1-20, and/or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of 1-20, and/or a pharmaceutically acceptable salts thereof to a subject.

In another of its aspects, there is provided a method of inhibiting a PI3K kinase comprising contacting the PI3K with a compound of any one of 1-20, and/or a pharmaceutically acceptable salts thereof.

In yet another of its aspects, there is provided a method of inhibiting a PI3K comprising causing a compound of any one of 1-20, and/or a pharmaceutically acceptable salts thereof, to be present in a subject in order to inhibit the PI3K in vivo.

In a further of its aspects, there is provided a method of inhibiting PI3K comprising administering a first compound to a subject that is converted in vivo to a second compound wherein the second compound inhibits the PI3K in vivo, the second compound being a compound according to any one of 1-20, and/or a pharmaceutically acceptable salts thereof.

In another of its aspects, there is provided a method of treating a disease state for which a PI3K possesses activity that contributes to the pathology and/or symptomology of the disease state, the method comprising causing a compound of any one of 1-20, and/or a pharmaceutically acceptable salts thereof, to be present in a subject in a therapeutically effective amount for the disease state.

In a further of its aspects, there is provided a method of treating a disease state for which a PI3K possesses activity that contributes to the pathology and/or symptomology of the disease state, the method comprising administering a first compound to a subject that is converted in vivo to a second compound wherein the second compound inhibits the PI3K in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the PI3K gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of 1-20, and/or a pharmaceutically acceptable salts thereof, in the manufacture of a medicament for inhibiting a PI3K.

In a further of its aspects, the present invention relates to the use of a compound according to any one of 1-20, and/or a pharmaceutically acceptable salts thereof, in the manufacture of a medicament for treating a disease state for which a PI3K possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers as used herein, refers to relatively non-toxic chemical compounds or agents that facilitate the incorporation of a compound into cells or tissues, which include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the abovementioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arable, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the disclosure may be administered as the sole active ingredient, or together with other drugs useful against neoplastic diseases or useful in immunomodulating regimens. For example, the compounds of the disclosure may be used in accordance with the disclosure in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. WIC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

EXAMPLES

Various methods may be developed for synthesizing a compound of formula (I) and/or a pharmaceutically acceptable salt thereof. Representative methods for synthesizing a compound of formula (I) and/or a pharmaceutically acceptable salt thereof are provided in the Examples. It is noted, however, that a compound of formula (I) and/or a pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of a compound of formula (I) and/or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (I) can also be prepared as a pharmaceutically acceptable acid addition salt by, for example, reacting the free base form of a compound with a pharmaceutically acceptable inorganic or organic acid. Alternatively, a pharmaceutically acceptable base addition salt of a compound of formula (I) can be prepared by, for example, reacting the free acid form of a compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of a compound of formula (I) and/or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution. Flash column chromatography was performed on silica gel (200-300 mesh, Branch of Qingdao Haiyang Chemical Co., Ltd).

Synthetic Schemes

A compound of formula I or II and/or a pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present disclosure are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As shown in the Scheme 1, the compounds of formula I can be synthesized from amine II and aryl or heteroaryl halide III, which are either known in the literature or may be prepared by a variety of methods familiar to those skilled in the art. Coupling of the amine II with halide III in the presence of a base such as DIPEA in a solvent such as IPA or under other coupling conditions known in the literature provide compounds of formula I.

Scheme 1

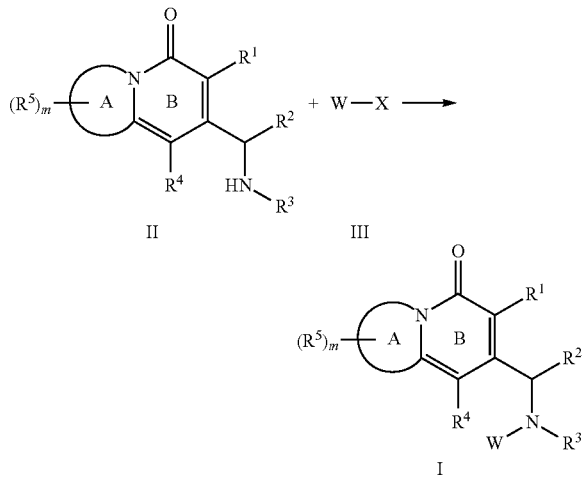

As an illustration of the preparation of intermediate II. One synthetic route of II is shown in Scheme 2. The preparation starts with II-a, which is commercially available or can be synthesized following the procedure known in the literature. Wittig reaction of II-a with Horner reagents such as II-b in the presence of a base such as NaH provides diester II-c. Heating of II-c with an acid such as poly phosphoric acid leads to pyridone II-d. Halogenation of II-d with reagents such as NBS or NIS followed by metal catalyzed coupling reactions, Suzuki coupling for example, gives II-f. Ester II-f can be converted into aldehyde II-h either by DIBAL-H reduction or via a sequence of $NaBH_4/CaCl_2$ reduction and $MnO_2$ oxidation. Grinard addition to aldehyde II-f provides alcohol II-i, the hydroxyl group of which can be transformed into an amine group to give Intermediate II as shown in Scheme 1. The hydroxy group of II-i can be converted into a leaving group by reacting with reagents such as MsCl or TosCl to give II j. Displacement of leaving group in II-j by nucleiphilic reagents such as amine or azide leads to intermediate II or azide II-k respectively. Reduction of azide II-k with a reducing reagent such as $Ph_3P$ gives intermediate II. Azide II-k can also be obtained via mitsunobo reaction of alcohol II-i with DPPA.

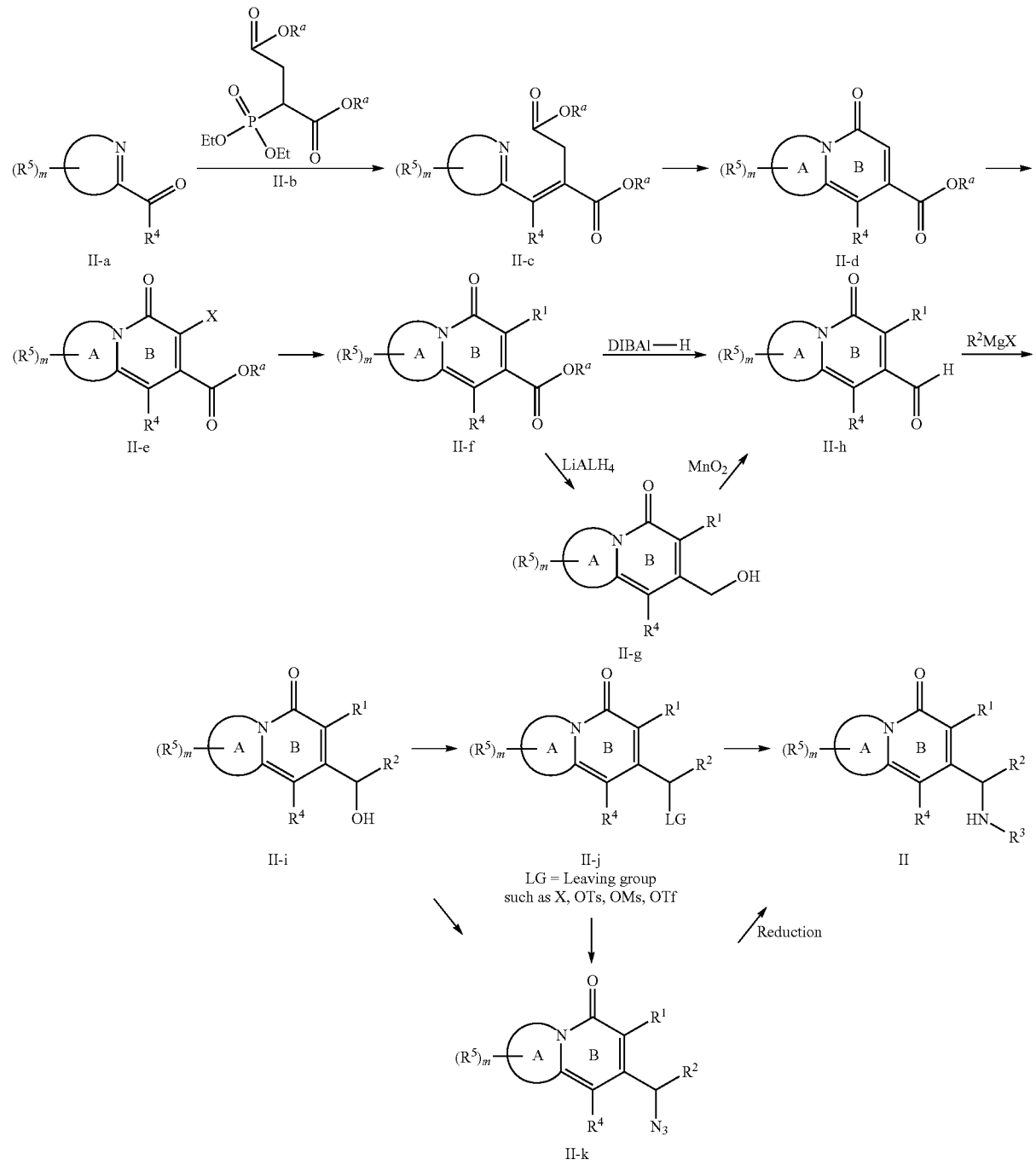

Scheme 2

Ra = Alkyl

A chiral resolution approach to get enantiomerically pure Intermediate II is outlined in Scheme 3. Coupling of amine II with enatiomerically pure O-Methylmandelic acid gives a mixture of diastereomers of II-j which can be separated either by column or recrystallization. Cleavage of the amide bond in II-j give enantiomerically pure intermediate II-R or II-S.

Scheme 4. Condensation of aldehyde II-h with (R) or (S)-tert-butansulfinamide in the presence of a base such as $Cs_2CO_3$ in a solvent such as DCM provides immine II-n. Grinard addition to immine II-n gives II-p which can be converted to enatiomerically pure intermediate II-R or II-S by treatment with aqueous HCl.

Scheme 3

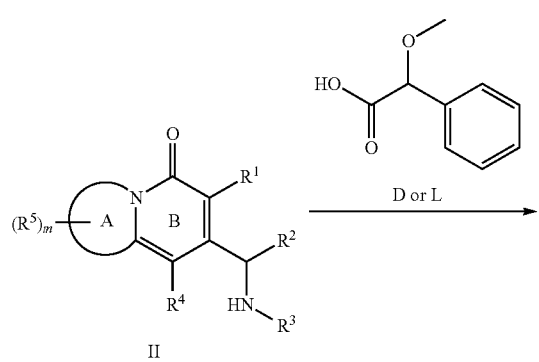

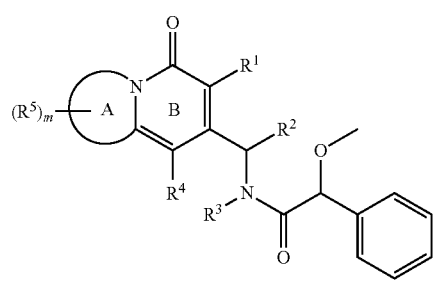

II-m
Diateromeric Mixtures

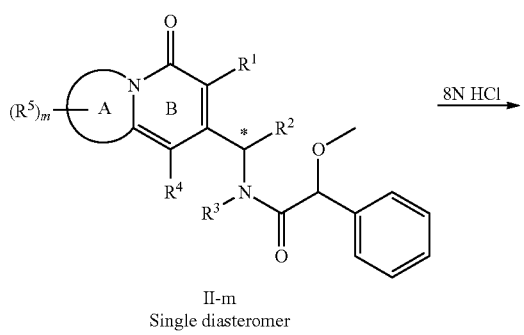

II-m
Single diasteromer

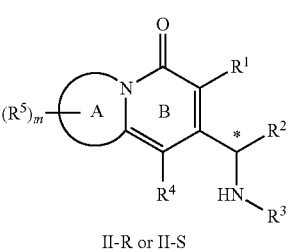

II-R or II-S

Alternatively, enantiomerically pure intermediate II-R or II-S can be synthesized through the procedure shown in

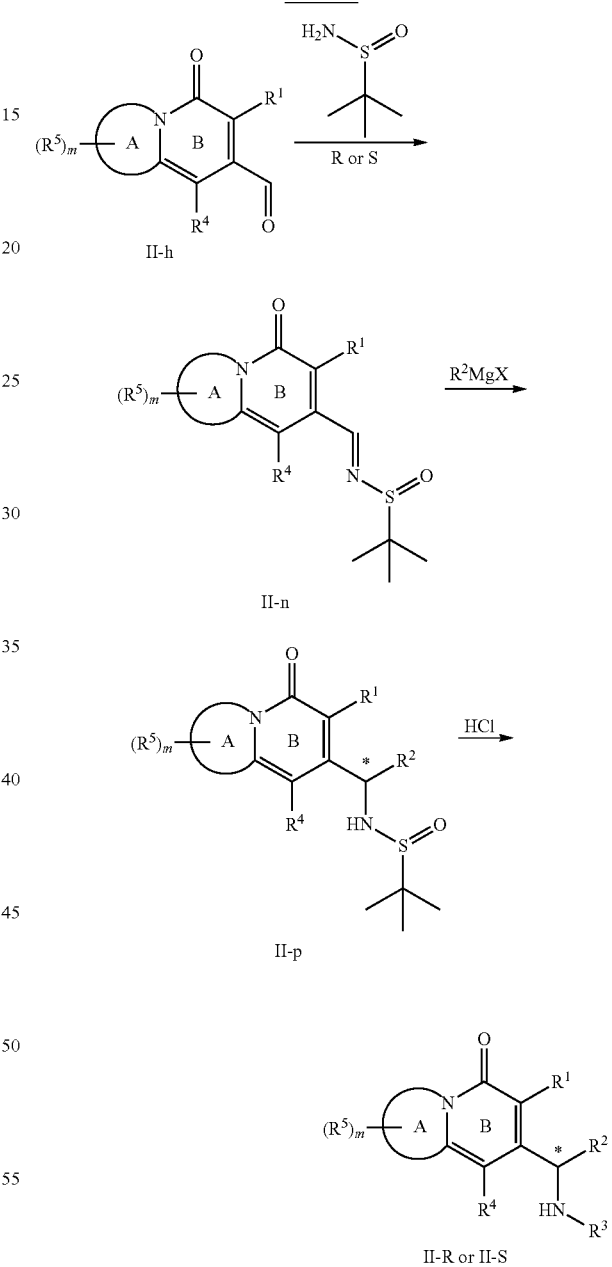

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1

7-(1-(9H-purin-6-ylamino)ethyl)-3-methyl-6-phenyl-5H-thiazolo[3,2-a]pyridin-5-one (1)

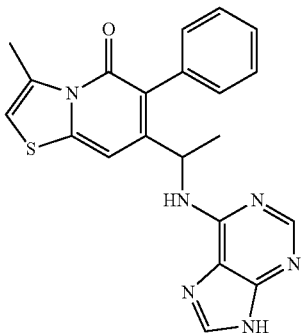

4-methylthiazole-2-carbaldehyde (1a)

4-methylthiazole-2-carbaldehyde (1a) was prepared according to the method described in WO2011138751.

dimethyl 2-(diethoxyphosphoryl)succinate (1b)

Dimethyl 2-(diethoxyphosphoryl)succinate (1b) was prepared according to the method described in *Eur. J. Med. Chem.* 2010, 45: 4403.

dimethyl 2-((4-methylthiazol-2-yl)methylene)succinate (1c)

To a solution of dimethyl 2-(diethoxyphosphoryl)succinate (1b) (0.56 g, 2.0 mmol) in THF (10 mL) was added NaH (60%, 0.092 g, 2.4 mmol) at 0° C., the mixture was stirred at 0~5° C. for 1 h. A solution of 4-methylthiazole-2-carbaldehyde (1a) (0.25 g, 2.0 mmol) in THF (2 mL) was added. The mixture was stirred at r.t. for 3 h. The reaction was quenched by saturated NH$_4$Cl aqueous solution (20 mL) and extracted with EtOAc (2×30 mL). The extracts were washed with saturated brine (30 mL), dried with Na$_2$SO$_4$ and concentrated. The residue was purified by flash column chromatography on silica gel eluting with PE/EtOAc (10:1) to give the title compound dimethyl 2-((4-methylthiazol-2-yl)methylene)succinate (1c). MS-ESI (m/z): 256 [M+I]$^+$.

methyl 3-methyl-5-oxo-5H-thiazolo[3,2-a]pyridine-7-carboxylate (1d)

A mixture of dimethyl 2-((4-methylthiazol-2-yl)methylene)succinate (1c) (3.77 g, 14.7 mmol) and PPA (50.0 g) was stirred at 80° C. overnight. The reaction mixture was poured onto 250 g ice and adjusted with Na$_2$CO$_3$ to pH=9~10. The mixture was extracted with DCM (3×100 mL). The extracts were washed with saturated brine (100 mL), dried with Na$_2$SO$_4$ and concentrated. The residue was purified by column chromatography on silica gel eluting with PE/EtOAc (10:1~2:1) to give the title compound methyl 3-methyl-5-oxo-5H-thiazolo[3,2-a]pyridine-7-carboxylate (1d). MS-ESI (m/z): 225 [M+1]$^+$.

methyl 6-iodo-3-methyl-5-oxo-5H-thiazolo[3,2-a]pyridine-7-carboxylate (1e)

To a solution of methyl 3-methyl-5-oxo-5H-thiazolo[3,2-a]pyridine-7-carboxylate (1d) (1.5 g, 6.7 mmol) in DCM (50 mL) was added NIS (0.9 g, 4 mmol). The mixture was stirred at r.t. for 3 h. Another portion of NIS (0.9 g, 4 mmol) was added and stirred at r.t. for 3 h, the final portion of NIS (0.2 g, 0.88 mmol) was added. The mixture was stirred at r.t. for another 1 h and diluted with DCM (50 mL), washed with saturated Na$_2$S$_2$O$_3$ aqueous solution (50 mL), saturated NaHCO$_3$ aqueous solution (50 mL) and saturated brine (50 mL), dried over Na$_2$SO$_4$. Filtered, and evaporated, the residue was purified by column chromatography on silica gel eluting with PE/EtOAc (10:1~5:1) to give title compound methyl 6-iodo-3-methyl-5-oxo-5H-thiazolo[3,2-a]pyridine-7-carboxylate (1e). MS-ESI (m/z): 350 [M+1]$^+$.

methyl 3-methyl-5-oxo-6-phenyl-5H-thiazolo[3,2-a]pyridine-7-carboxylate (1f)

A mixture of methyl 6-iodo-3-methyl-5-oxo-5H-thiazolo[3,2-a]pyridine-7-carboxylate (1e) (0.17 g, 0.5 mmol), commercial available phenylboronic acid (0.12 g, 1.0 mmol) and Cs$_2$CO$_3$ (0.65 g, 2.0 mmol) in dioxane (6 mL) was degassed, Pd(PPh$_3$)$_2$Cl$_2$ (0.07 g, 0.1 mmol) was added, degassed again. The mixture was stirred at 85° C. for 5 h under N$_2$ atmosphere. The mixture was cooled to r.t. and concentrate. The residue was purified by column chromatography on silica gel eluting with PE/EtOAc (10:1~4:1) to give the title compound methyl 3-methyl-5-oxo-6-phenyl-5H-thiazolo[3,2-a]pyridine-7-carboxylate (14 MS-ESI (m/z): 300 [M+1]$^+$.

3-methyl-5-oxo-6-phenyl-5H-thiazolo[3,2-a]pyridine-7-carbaldehyde (1g)

To a solution of methyl 3-methyl-5-oxo-6-phenyl-5H-thiazolo[3,2-a]pyridine-7-carboxylate (1f) (0.36 g, 1.2 mmol) in DCM (15 mL) was added DIBAl-H (4 mL, 6 mmol) at −78° C. The mixture was stirred at −78~−60° C. for 0.5 h and quenched by MeOH (5 mL) at −78° C. 15% NaOH aqueous solution was added and stirred at r.t. for 0.5 h. The mixture was extracted by DCM (2×50 mL), the extracts were washed with brine (50 mL), dried with Na$_2$SO$_4$. Filtered, and evaporated, the residue was purified by column chromatography on silica gel eluting with PE/EtOAc (10:1~2:1) to give title compound 3-methyl-5-oxo-6-phenyl-5H-thiazolo[3,2-a]pyridine-7-carbaldehyde (1g). MS-ESI (m/z): 270 [M+1]$^+$.

7-(1-hydroxyethyl)-3-methyl-6-phenyl-5H-thiazolo[3,2-a]pyridin-5-one (1h)

To a solution of 3-methyl-5-oxo-6-phenyl-5H-thiazolo[3,2-a]pyridine-7-carbaldehyde (1g) (0.15 g, 0.6 mmol) in THF (10 mL) was added MeMgBr (0.8 mL, 2.4 mmol) at −78° C. The mixture was warmed to r.t. slowly and stirred at r.t. for 1 h. The reaction was quenched by saturated NH$_4$Cl aqueous solution (15 mL) at 0° C. and extracted by EtOAc (2×50 mL). The extracts were washed with brine (50 mL), dried with Na$_2$SO$_4$, filtered, and evaporated. The residue was purified by column chromatography on silica gel eluting with PE/EtOAc (2:1) to give title compound 7-(1-hydroxyethyl)-3-methyl-6-phenyl-5H-thiazolo[3,2-a]pyridin-5-one (1h). MS-ESI (m/z): 286 [M+H]$^+$.

1-(3-methyl-5-oxo-6-phenyl-5H-thiazolo[3,2-a]pyridin-7-yl)ethyl methanesulfonate (1i)

To a solution of 7-(1-hydroxyethyl)-3-methyl-6-phenyl-5H-thiazolo[3,2-a]pyridin-5-one (1h) (0.065 g, 0.23 mmol) in DCM (5 mL) was added TEA (0.101 g, 1 mmol) at 0° C. followed by MSCl (0.06 g, 0.5 mmol). The mixture was stirred at r.t. for 2 h and quenched by water (20 mL) at 0° C. The mixture was extracted by DCM (25 mL), washed with brine (15 mL), dried with $Na_2SO_4$. Filtered, and evaporated to give the crude product of 1-(3-methyl-5-oxo-6-phenyl-5H-thiazolo[3,2-a]pyridin-7-yl)ethyl methanesulfonate (1i), which was used for next step directly. MS-ESI (m/z): 364 [M+H]$^+$.

7-(1-aminoethyl)-3-methyl-6-phenyl-5H-thiazolo[3,2-a]pyridin-5-one (1j)

To a solution of 1-(3-methyl-5-oxo-6-phenyl-5H-thiazolo[3,2-a]pyridin-7-yl)ethyl methanesulfonate (1i) (0.075 g, 0.2 mmol) in IPA (5 mL) was bubbled $NH_3$ at 0° C. for 0.5 h, the mixture was stirred at 70° C. in sealed tube overnight. Concentrated, the crude product was purified by column chromatography on silica gel eluting with DCM/MeOH (20:1) to give title compound 7-(1-aminoethyl)-3-methyl-6-phenyl-5H-thiazolo[3,2-a]pyridin-5-one (1j). MS-ESI (m/z): 285 [M+H]$^+$.

7-(1-(9H-purin-6-ylamino)ethyl)-3-methyl-6-phenyl-5H-thiazolo[3,2-a]pyridin-5-one (1)

A mixture of 7-(1-aminoethyl)-3-methyl-6-phenyl-5H-thiazolo[3,2-a]pyridin-5-one (1j) (0.02 g, 0.08 mmol), commercial available 6-chloro-9H-purine (0.015 g, 0.1 mmol) and DIEA (0.065 g, 0.5 mmol) in IPA (2 mL) was stirred at 100° C. in sealed tube for 24 h. The mixture was cooled to r.t. and concentrate. The residue was purified by preparative TLC eluting with DCM/MeOH (20:1) to give the title compound 7-(1-(9H-purin-6-ylamino)ethyl)-3-methyl-6-phenyl-5H-thiazolo[3,2-a]pyridin-5-one (1). MS-ESI (m/z): 403 [M+H]$^+$.

Example 2

7-(1-(9H-purin-6-ylamino)propyl)-3-methyl-6-phenyl-5H-thiazolo[3,2-a]pyridin-5-one (2)

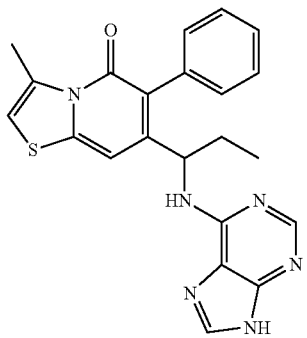

7-(1-hydroxyallyl)-3-methyl-6-phenyl-5H-thiazolo[3,2-a]pyridin-5-one (2a)

The title compound 7-(1-hydroxyallyl)-3-methyl-6-phenyl-5H-thiazolo[3,2-a]pyridin-5-one (2a) was prepared by using the same procedure as described for 1h by replacing methyl magnesium bromide with vinyl magnesium bromide. MS-ESI (m/z): 298 [M+1]$^+$.

7-(1-hydroxypropyl)-3-methyl-6-phenyl-5H-thiazolo[3,2-a]pyridin-5-one (2b)

A mixture of 7-(1-hydroxyallyl)-3-methyl-6-phenyl-5H-thiazolo[3,2-a]pyridin-5-one (2a) (0.033 g, 0.11 mmol), Pd/C (10%, 0.015 g) and cyclohexa-1,4-diene (0.08 g, 1 mmol) in EtOH (2 mL) was stirred at 65° C. for 48 h. The mixture was cooled to r.t. and filtered by celite. The filtrate was concentrate, purified by preparative TLC eluting with PE/EA (1:1) to give the title compound 7-(1-hydroxypropyl)-3-methyl-6-phenyl-5H-thiazolo[3,2-a]pyridin-5-one (2b). MS-ESI (m/z): 300 [M+1]$^+$.

1-(3-methyl-5-oxo-6-phenyl-5H-thiazolo[3,2-a]pyridin-7-yl)propyl methanesulfonate (2c)

The title compound 1-(3-methyl-5-oxo-6-phenyl-5H-thiazolo[3,2-a]pyridin-7-yl)propyl methanesulfonate (2c) was prepared by using the same procedure as described for 1i by replacing 7-(1-hydroxyethyl)-3-methyl-6-phenyl-5H-thiazolo[3,2-a]pyridin-5-one (1h) with 7-(1-hydroxypropyl)-3-methyl-6-phenyl-5H-thiazolo[3,2-a]pyridin-5-one (2b). MS-ESI (m/z): 378 [M+1]$^+$.

7-(1-aminopropyl)-3-methyl-6-phenyl-5H-thiazolo[3,2-a]pyridin-5-one (2d)

The title compound 7-(1-aminopropyl)-3-methyl-6-phenyl-5H-thiazolo[3,2-a]pyridin-5-one (2d) was prepared by using the same procedure as described for 1j by replacing 1-(3-methyl-5-oxo-6-phenyl-5H-thiazolo[3,2-a]pyridin-7-yl)ethyl methanesulfonate (1i) with 1-(3-methyl-5-oxo-6-phenyl-5H-thiazolo[3,2-a]pyridin-7-yl)propyl methanesulfonate (2c). MS-ESI (m/z): 299 [M+1]$^+$.

7-(1-(9H-purin-6-ylamino)propyl)-3-methyl-6-phenyl-5H-thiazolo[3,2-a]pyridin-5-one (2)

A mixture of 7-(1-aminopropyl)-3-methyl-6-phenyl-5H-thiazolo[3,2-a]pyridin-5-one (2d) (0.015 g, 0.05 mmol), commercial available 6-chloro-9H-purine (0.01 g, 0.06 mmol) and DIEA (0.065 g, 0.5 mmol) in t-BuOH (1 mL) was stirred at 80° C. for 48 h. The mixture was cooled to r.t. and concentrate. The residue was purified by preparative TLC eluting with DCM/MeOH (10:1) to give the title compound 7-(1-(9H-purin-6-ylamino) propyl)-3-methyl-6-phenyl-5H-thiazolo[3,2-a]pyridin-5-one (2). MS-ESI (m/z): 417 [M+1]$^+$.

Example 3

2-(1-(9H-purin-6-ylamino)ethyl)-3-phenyl-4H-quinolizin-4-one (3)

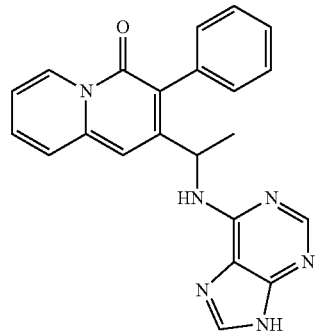

dimethyl 2-(pyridin-2-ylmethylene)succinate (3a)

The title compound dimethyl 2-(pyridin-2-ylmethylene)succinate (3a) was prepared by using the same procedure as described for 1c by replacing 4-methylthiazole-2-carbaldehyde (1a) with picolinaldehyde. MS-ESI (m/z): 236 [M+1]$^+$.

methyl 4-oxo-4H-quinolizine-2-carboxylate (3b)

A mixture of dimethyl 2-(pyridin-2-ylmethylene)succinate (3a) (2.35 g, 10 mmol) and PTSa (0.2 g) in toluene (25 mL) was stirred at 110° C. for 7 h. The reaction mixture was cooled to r.t. and concentrated. The residue was diluted with DCM (100 mL), washed with saturated NaHCO$_3$ aqueous solution (50 mL), brine (50 mL), dried over Na$_2$SO$_4$ and concentrated. The residue was recrystallized with PE/EtOAc to give the title compound methyl 4-oxo-4H-quinolizine-2-carboxylate (3b). MS-ESI (m/z): 204 [M+1]$^+$.

methyl 3-iodo-4-oxo-4H-quinolizine-2-carboxylate (3c)

The title compound methyl 3-iodo-4-oxo-4H-quinolizine-2-carboxylate (3c) was prepared by using the same procedure as described for 1e by replacing methyl 3-methyl-5-oxo-5H-thiazolo[3,2-a]pyridine-7-carboxylate (1d) with 4-oxo-4H-quinolizine-2-carboxylate (3b). MS-ESI (m/z): 330 [M+1]$^+$.

methyl 4-oxo-3-phenyl-4H-quinolizine-2-carboxylate (3d)

The title compound methyl 4-oxo-3-phenyl-4H-quinolizine-2-carboxylate (3d) was prepared by using the same procedure as described for 1f by replacing methyl 6-iodo-3-methyl-5-oxo-5H-thiazolo[3,2-a]pyridine-7-carboxylate (1e) with methyl 3-iodo-4-oxo-4H-quinolizine-2-carboxylate (3c). MS-ESI (m/z): 280 [M+1]$^+$.

2-(hydroxymethyl)-3-phenyl-4H-quinolizin-4-one (3e)

To a solution of methyl 4-oxo-3-phenyl-4H-quinolizine-2-carboxylate (3d) (0.20 g, 0.71 mmol) in THF (15 mL) was added CaCl$_2$ (0.10 g, 0.9 mmol) followed by NaBH$_4$ (0.60 g, 15 mmol). The mixture was stirred at 70° C. for 3.5 h and quenched by ice water (20 mL) at 0° C. The mixture was extracted by EtOAc (2×50 mL), the extracts were washed with brine (50 mL), dried over Na$_2$SO$_4$. Filtered and concentrate, the residue was purified by column chromatography on silica gel eluting with PE/EtOAc (1:1) to give title compound 2-(hydroxymethyl)-3-phenyl-4H-quinolizin-4-one (3e). MS-ESI (m/z): 252 [M+1]$^+$.

4-oxo-3-phenyl-4H-quinolizine-2-carbaldehyde (3f)

A mixture of 2-(hydroxymethyl)-3-phenyl-4H-quinolizin-4-one (3e) (0.10 g, 0.4 mmol) and MnO$_2$ (1.9 g, 20 mmol) in dioxane (8 mL) was stirred at 90° C. for 2.5 h. The mixture was filtered through celite, the filtrate was concentrated to give the crude product of 4-oxo-3-phenyl-4H-quinolizine-2-carbaldehyde (3f), which was used for next step directly. MS-ESI (m/z): 250 [M+1]$^+$.

2-(1-hydroxyethyl)-3-phenyl-4H-quinolizin-4-one (3g)

The title compound 2-(1-hydroxyethyl)-3-phenyl-4H-quinolizin-4-one (3g) was prepared by using the same procedure as described for 1h by replacing 3-methyl-5-oxo-6-phenyl-5H-thiazolo[3,2-a]pyridine-7-carbaldehyde (1g) with 4-oxo-3-phenyl-4H-quinolizine-2-carbaldehyde (3f). MS-ESI (m/z): 266 [M+1]$^+$.

1-(4-oxo-3-phenyl-4H-quinolizin-2-yl)ethyl methanesulfonate (3h)

The title compound 1-(4-oxo-3-phenyl-4H-quinolizin-2-yl)ethyl methanesulfonate (3h) was prepared by using the same procedure as described for 1i by replacing 7-(1-hydroxyethyl)-3-methyl-6-phenyl-5H-thiazolo[3,2-a]pyridin-5-one (1h) with 2-(1-hydroxyethyl)-3-phenyl-4H-quinolizin-4-one (3g). MS-ESI (m/z): 344 [M+1]$^+$.

2-(1-aminoethyl)-3-phenyl-4H-quinolizin-4-one (3i)

The title compound 2-(1-aminoethyl)-3-phenyl-4H-quinolizin-4-one (3i) was prepared by using the same procedure as described for 1j by replacing 1-(3-methyl-5-oxo-6-phenyl-5H-thiazolo[3,2-a]pyridin-7-yl)ethyl methanesulfonate (1i) with 1-(4-oxo-3-phenyl-4H-quinolizin-2-yl)ethyl methanesulfonate (3h). MS-ESI (m/z): 265 [M+1]$^+$.

2-(1-(9H-purin-6-ylamino)ethyl)-3-phenyl-4H-quinolizin-4-one (3)

The title compound 2-(1-(9H-purin-6-ylamino)ethyl)-3-phenyl-4H-quinolizin-4-one (3) was prepared by using the same procedure as described for 1 by replacing 7-(1-aminoethyl)-3-methyl-6-phenyl-5H-thiazolo[3,2-a]pyridin-5-one (1j) with 2-(1-aminoethyl)-3-phenyl-4H-quinolizin-4-one (3i). MS-ESI (m/z): 383 [M+1]$^+$.

Example 4

2-(1-(9H-purin-6-ylamino)propyl)-3-phenyl-4H-quinolizin-4-one (4)

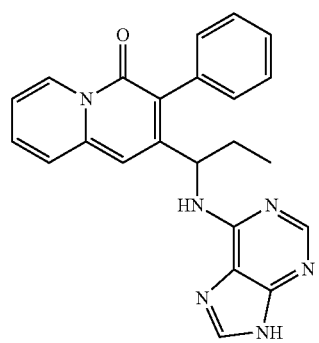

4

2-(1-hydroxypropyl)-3-phenyl-4H-quinolizin-4-one (4a)

The title compound 2-(1-hydroxypropyl)-3-phenyl-4H-quinolizin-4-one (4a) was prepared by using the same procedure as described for 3g by replacing methyl magnesium bromide with ethyl magnesium bromide. MS-ESI (m/z): 280 [M+1]$^+$.

1-(4-oxo-3-phenyl-4H-quinolizin-2-yl)propyl methanesulfonate (4b)

The title compound 1-(4-oxo-3-phenyl-4H-quinolizin-2-yl)propyl methanesulfonate (4b) was prepared by using the same procedure as described for 1i by replacing 7-(1-hydroxyethyl)-3-methyl-6-phenyl-5H-thiazolo[3,2-a]pyridin-5-one (1h) with 2-(1-hydroxypropyl)-3-phenyl-4H-quinolizin-4-one (4a). MS-ESI (m/z): 358 [M+1]$^+$.

2-(1-aminopropyl)-3-phenyl-4H-quinolizin-4-one (4c)

The title compound 2-(1-aminopropyl)-3-phenyl-4H-quinolizin-4-one (4c) was prepared by using the same procedure as described for 1j by replacing 1-(3-methyl-5-oxo-6-phenyl-5H-thiazolo[3,2-a]pyridin-7-yl)ethyl methanesulfonate (1i) with 1-(4-oxo-3-phenyl-4H-quinolizin-2-yl)propyl methanesulfonate (4b). MS-ESI (m/z): 378 [M+1]$^+$.

2-(1-(9H-purin-6-ylamino)propyl)-3-phenyl-4H-quinolizin-4-one (4)

The title compound 2-(1-(9H-purin-6-ylamino)propyl)-3-phenyl-4H-quinolizin-4-one (4) was prepared by using the same procedure as described for 1 by replacing 7-(1-aminoethyl)-3-methyl-6-phenyl-5H-thiazolo[3,2-a]pyridin-5-one (1j) with 2-(1-aminopropyl)-3-phenyl-4H-quinolizin-4-one (4c). MS-ESI (m/z): 397 [M+1]$^+$.

Example 5

7-(1-((9H-purin-6-yl)amino)ethyl)-6-(4-fluorophenyl)-3-methyl-5H-thiazolo[3,2-a]pyridin-5-one (5)

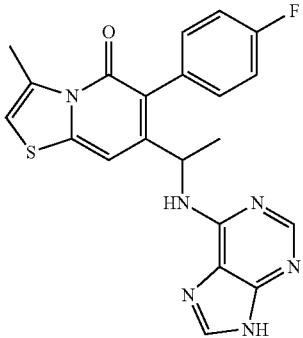

methyl 6-(4-fluorophenyl)-3-methyl-5-oxo-5H-thiazolo[3,2-a]pyridine-7-carboxylate (5a)

The title compound methyl 6-(4-fluorophenyl)-3-methyl-5-oxo-5H-thiazolo[3,2-a]pyridine-7-carboxylate (5a) was prepared according to the synthetic method of 1f by replacing phenylboronic acid with (4-fluorophenyl)boronic acid. MS-ESI (m/z): 318 [M+1]$^+$.

6-(4-fluorophenyl)-3-methyl-5-oxo-5H-thiazolo[3,2-a]pyridine-7-carbaldehyde (5b)

The title compound 6-(4-fluorophenyl)-3-methyl-5-oxo-5H-thiazolo[3,2-a]pyridine-7-carbaldehyde (5b) was prepared according to the synthetic method of 1g by replacing methyl 3-methyl-5-oxo-6-phenyl-5H-thiazolo[3,2-a]pyridine-7-carboxylate (1f) with methyl 6-(4-fluorophenyl)-3-methyl-5-oxo-5H-thiazolo[3,2-a]pyridine-7-carboxylate (5a). MS-ESI (m/z): 288 [M+1]$^+$.

1-(6-(4-fluorophenyl)-3-methyl-5-oxo-5H-thiazolo[3,2-a]pyridin-7-yl)ethyl methanesulfonate (5c)

The title compound 1-(6-(4-fluorophenyl)-3-methyl-5-oxo-5H-thiazolo[3,2-a]pyridin-7-yl)ethyl methanesulfonate (5c) was prepared according to the synthetic method of 1i by replacing 3-methyl-5-oxo-6-phenyl-5H-thiazolo[3,2-a]pyridine-7-carbaldehyde (1g) with 6-(4-fluorophenyl)-3-methyl-5-oxo-5H-thiazolo[3,2-a]pyridine-7-carbaldehyde (5b). MS-ESI (m/z): 382 [M+1]$^+$.

7-(1-azidoethyl)-6-(4-fluorophenyl)-3-methyl-5H-thiazolo[3,2-a]pyridin-5-one (5d)

A mixture of 1-(6-(4-fluorophenyl)-3-methyl-5-oxo-5H-thiazolo[3,2-a]pyridin-7-yl)ethyl methanesulfonate (5c) (0.266 g, 0.7 mmol) and NaN$_3$ (0.13 g, 2.1 mmol) in DMF (3 mL) was stirred at 30° C. overnight. The mixture was diluted with water (20 mL), extracted with EtOAc (2×20 mL). The organic phase was washed with brine (20 mL), dried over Na$_2$SO$_4$ and concentrated to give the crude product of 7-(1-azidoethyl)-6-(4-fluorophenyl)-3-methyl-5H-thiazolo[3,2-a]pyridin-5-one (5d), which was used for next step directly. MS-ESI (m/z): 329 [M+1]$^+$.

7-(1-aminoethyl)-6-(4-fluorophenyl)-3-methyl-5H-thiazolo[3,2-a]pyridin-5-one (5e)

A solution of 7-(1-azidoethyl)-6-(4-fluorophenyl)-3-methyl-5H-thiazolo[3,2-a]pyridin-5-one (5d) (0.24 g, 0.73 mmol) and PPh$_3$ (0.57 g, 2.2 mmol) in THF (5 mL) and water (0.13 g) was stirred at 40° C. overnight, concentrated, the residue was purified to give 7-(1-aminoethyl)-6-(4-fluorophenyl)-3-methyl-5H-thiazolo[3,2-a]pyridin-5-one (5e). MS-ESI (m/z): 303 [M+1]$^+$.

(2R)-N-(1-(6-(4-fluorophenyl)-3-methyl-5-oxo-5H-thiazolo[3,2-a]pyridin-7-yl)ethyl)-2-methoxy-2-phenylacetamide (5f)

A mixture of (R)-2-methoxy-2-phenylacetic acid (0.15 g, 0.9 mmol), EDCI (0.24 g, 1.2 mmol), HOBT (0.1 g, 0.9 mmol) and DIPEA (0.36 g, 3.0 mmol) in DMF (6 mL) was stirred at r.t. for 0.5 h, and then, a solution of 7-(1-aminoethyl)-6-(4-fluorophenyl)-3-methyl-5H-thiazolo[3,2-a]pyridin-5-one (5e) (0.18 g, 0.6 mmol) in THF (1.0 mL) was added. It was stirred at r.t for 2 h, diluted with water (50 mL), and extracted with EA (50 mL×2). The organic phase was washed with 10% citric acid (20 mL), a.q NaHCO$_3$ (20 mL) and brine (20 mL), dried, concentrated and purified by TLC (PE:THF=2:1) to give (2R)-N-(1-(6-(4-fluorophenyl)-3-methyl-5-oxo-5H-thiazolo[3,2-a]pyridin-7-yl)ethyl)-2-methoxy-2-phenylacet amide (5f-a and 5f-b). MS-ESI (m/z): 451 [M+1]$^+$.

7-(1-aminoethyl)-6-(4-fluorophenyl)-3-methyl-5H-thiazolo[3,2-a]pyridin-5-one (5g)

A solution of 5f-a (0.065 g, 0.144 mmol) in 8 N HCl (6 mL) was stirred for 4 h at 100° C., then, cooled to r.t., diluted with water (20 mL), and extracted with DCM (2×20 mL). The aqueous layer was adjusted to pH=11-12 by 2 N NaOH, and extracted with DCM:IPA=4:1 (3×30 mL). The organic phase was washed with brine (20 mL), dried over Na$_2$SO$_4$, and concentrated to give 7-(1-aminoethyl)-6-(4-fluorophenyl)-3-methyl-5H-thiazolo[3,2-a]pyridin-5-one (5g), which was used for next step directly. MS-ESI (m/z): 303 [M+1]$^+$.

7-(1 purin-6-yl)amino)ethyl)-6-(4-fluorophenyl)-3-methyl-5H-thiazolo[3,2-a]pyridin-5-one (5)

The title compound 7-(1-((9H-purin-6-yl)amino)ethyl)-6-(4-fluorophenyl)-3-methyl-5H-thiazolo[3,2-a]pyridin-5-one (5) was prepared according to the synthetic method of 1 by replacing 7-(1-aminoethyl)-3-methyl-6-phenyl-5H-thiazolo[3,2-a]pyridin-5-one (1j) with 7-(1-aminoethyl)-6-(4-fluorophenyl)-3-methyl-5H-thiazolo[3,2-a]pyridin-5-one (5g). MS-ESI (m/z): 421 [M+1]$^+$.

Example 6

7-(1-((9H-purin-6-yl)amino)propyl)-6-(4-fluorophenyl)-3-methyl-5H-thiazolo[3,2-a]pyridin-5-one (6)

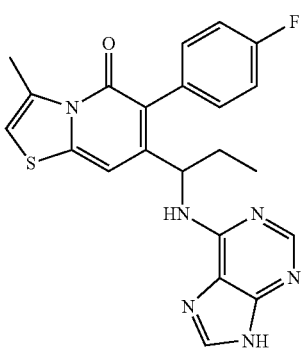

6

6-(4-fluorophenyl)-7-(1-hydroxypropyl)-3-methyl-5H-thiazolo[3,2-a]pyridin-5-one (6a)

The title compound 6-(4-fluorophenyl)-7-(1-hydroxypropyl)-3-methyl-5H-thiazolo[3,2-a]pyridin-5-one (6a) was prepared according to the synthetic method of 2b by replacing 3-methyl-5-oxo-6-phenyl-5H-thiazolo[3,2-a]pyridine-7-carbaldehyde (1g) with 6-(4-fluorophenyl)-3-methyl-5-oxo-5H-thiazolo[3,2-a]pyridine-7-carbaldehyde (5b). MS-ESI (m/z): 316 [M+1]$^+$.

1-(6-(4-fluorophenyl)-3-methyl-5-oxo-5H-thiazolo[3,2-a]pyridin-7-yl)propyl methanesulfonate (6b)

The title compound 1-(6-(4-fluorophenyl)-3-methyl-5-oxo-5H-thiazolo[3,2-a]pyridin-7-yl)propyl methanesulfonate (6b) was prepared according to the synthetic method of 2c by replacing 7-(1-hydroxyallyl)-3-methyl-6-phenyl-5H-thiazolo[3,2-a]pyridin-5-one (2a) with 6-(4-fluorophenyl)-7-(1-hydroxypropyl)-3-methyl-5H-thiazolo[3,2-a]pyridin-5-one (6a). MS-ESI (m/z): 396 [M+1]$^+$

7-(1-((9H-purin-6-yl)amino)propyl)-6-(4-fluorophenyl)-3-methyl-5H-thiazolo[3,2-a]pyridin-5-one (6)

The title compound 7-(149H-purin-6-yl)amino)propyl)-6-(4-fluorophenyl)-3-methyl-5H-thiazolo[3,2-a]pyridin-5-one (6) was prepared according to the synthetic method of 5 by replacing 1-(6-(4-fluorophenyl)-3-methyl-5-oxo-5H-thiazolo[3,2-a]pyridin-7-yl)ethyl methanesulfonate (5c) with 1-(6-(4-fluorophenyl)-3-methyl-5-oxo-5H-thiazolo[3,2-a]pyridin-7-yl)propyl methanesulfonate (6b). MS-ESI (m/z): 435 [M+1]$^+$ Following essentially the same procedures described for Examples 5, Examples 7-11 listed in Table 1 were prepared starting from the properly substituted thioazoles and using the appropriate Grinard reagents either commercially available or readily available by methods known in the art.

TABLE 1

| EXAMPLE | STRUCTURE | NAME | DATA |
|---|---|---|---|
| 7 | 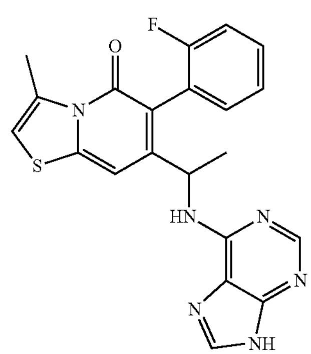 [SMILES: Cc1csc2cc(C(C)Nc3ncnc4[nH]cnc34)c(-c3ccccc3F)c(=O)n12] | 7-(1-((9H-purin-6-yl)amino)ethyl)-6-(2-fluorophenyl)-3-methyl-5H-thiazolo[3,2-a]pyridin-5-one | MS-ESI (m/z): 421 [M + 1]$^+$ |

TABLE 1-continued

| EXAMPLE | STRUCTURE | NAME | DATA |
|---|---|---|---|
| 8 | 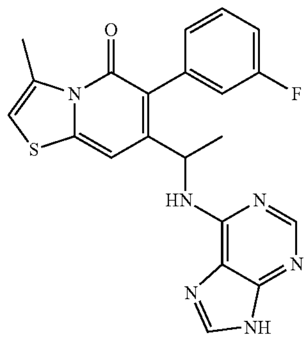 [SMILES: Cc1csc2cc(C(C)Nc3ncnc4[nH]cnc34)c(-c3cccc(F)c3)c(=O)n12] | 7-(1-((9H-purin-6-yl)amino)ethyl)-6-(3-fluorophenyl)-3-methyl-5H-thiazolo[3,2-a]pyridin-5-one | MS-ESI (m/z): 421 [M + 1]+ |
| 9 | 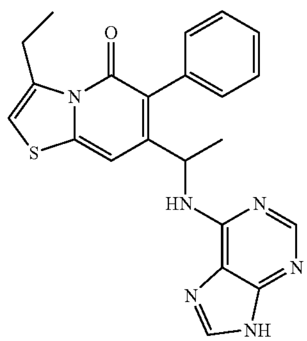 [SMILES: CCc1csc2cc(C(C)Nc3ncnc4[nH]cnc34)c(-c3ccccc3)c(=O)n12] | 7-(1((9H-purin-6-yl)amino)ethyl)-3-ethyl-6-phenyl-5H-thiazolo[3,2-a]pyridin-5-one | MS-ESI (m/z): 417 [M + 1]+ |
| 10 | 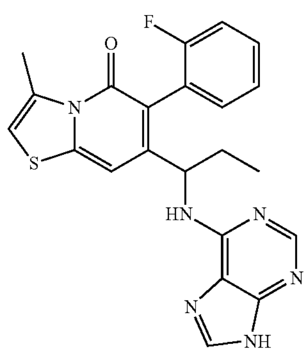 [SMILES: CCC(Nc1ncnc2[nH]cnc12)c1cc2scc(C)n2c(=O)c1-c1ccccc1F] | 7-(1-((9H-purin-6-yl)amino)propyl)-6-(2-fluorophenyl)-3-methyl-5H-thiazolo[3,2-a]pyridin-5-one | MS-ESI (m/z): 435 [M + 1]+ |
| 11 | 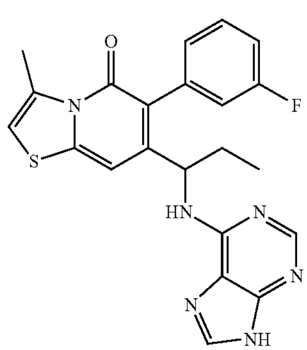 [SMILES: CCC(Nc1ncnc2[nH]cnc12)c1cc2scc(C)n2c(=O)c1-c1cccc(F)c1] | 7-(1((9H-purin-6-yl)amino)propyl)-6-(3-fluorophenyl)-3-methyl-5H-thiazolo[3,2-a]pyridin-5-one | MS-ESI (m/z): 435 [M + 1]+ |

Example 12

7-(1-((9H-purin-6-yl)amino)ethyl)-3-chloro-6-(3-fluorophenyl)-5H-thiazolo[3,2-a]pyridin-5-one (12)

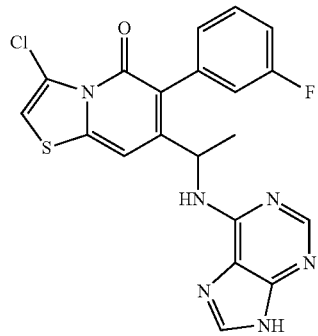

(4-chlorothiazol-2-yl)methanol (12a)

(4-chlorothiazol-2-yl)methanol (12a) was prepared according to the method described in WO2013149362.

4-chlorothiazole-2-carbaldehyde (12b)

To a solution of (4-chlorothiazol-2-yl)methanol (12a) (1.93 g, 12.95 mmol) in DCM (20 mL) was added DMP (6.04 g, 14.25 mol) at 0-5° C., stirred for 2-4 h at the same temperature, diluted with of DCM (50 mL), washed with saturated NaHCO$_3$ aqueous solution (50 mL), dried over Na$_2$SO$_4$, and concentrated. The residue was purified by column chromatography on silica gel eluting with PE/EtOAc (20:1) to give 4-chlorothiazole-2-carbaldehyde (12b). MS-ESI (m/z): 148,150 [M+1]$^+$

3-chloro-6-(3-fluorophenyl)-5-oxo-5H-thiazolo[3,2-a]pyridine-7-carbaldehyde (12c)

The title compound 3-chloro-6-(3-fluorophenyl)-5-oxo-5H-thiazolo[3,2-a]pyridine-7-carbaldehyde (12c) was prepared according to the synthetic method of 1g by replacing 4-methylthiazole-2-carbaldehyde (1a) with 4-chlorothiazole-2-carbaldehyde (12b). MS-ESI (m/z): 308,310 [M+1]$^+$.

(E)-N-((3-chloro-6-(3-fluorophenyl)-5-oxo-5H-thiazolo[3,2-a]pyridin-7-yl)methylene)-2-methylpropane-2-sulfinamide (12d)

A mixture of 3-chloro-6-(3-fluorophenyl)-5-oxo-5H-thiazolo[3,2-a]pyridine-7-carbaldehyde (12c) (3.0 g, 10.0 mmol), (S)-tert-butansulfinamide (1.815 g, 15.0 mmol) and Cs$_2$CO$_3$ (9.61 g, 30.0 mol) in DCM (80 mL) was stirred at r.t. for 2 h. The mixture was washed with water (80 mL), and the organic phase was washed with brine (50 mL), dried over Na$_2$SO$_4$ and concentrated. The residue was purified by column chromatography on silica gel eluting with EtOAc/PE (3:1) to give (E)-N-((3-chloro-6-(3-fluorophenyl)-5-oxo-5H-thiazolo[3,2-a]pyridin-7-yl)methylene)-2-methylpropane-2-sulfinamide (12d). MS-ESI (m/z): 411,413 [M+1]$^+$.

N-(1-(3-chloro-6-(3-fluorophenyl)-5-oxo-5H-thiazolo[3,2-a]pyridin-7-yl)ethyl)-2-methylpropane-2-sulfinamide (12e)

To a solution of (E)-N-((3-chloro-6-(3-fluorophenyl)-5-oxo-5H-thiazolo[3,2-a]pyridin-7-yl)methylene)-2-methylpropane-2-sulfinamide (12d) (3.1 g, 7.54 mmol) in THF (80 mL) was added methylmagnesium chloride (20.0 mL, 46.5 mmol) dropwise at −78° C. The mixture was stirred for 1.5 h at the same temperature and water was added. The mixture was extracted with EA (2×100 mL). The organic phase was washed with brine (50 mL), dried over Na$_2$SO$_4$, and concentrated. The residue was purified by column chromatography on silica gel eluting with EtOAc/DCM (1:1) to give N-(1-(3-chloro-6-(3-fluorophenyl)-5-oxo-5H-thiazolo[3,2-a]pyridin-7-yl)ethyl)-2-methylpropane-2-sulfinamide (12e). MS-ESI (m/z): 427,429 [M+1]$^+$.

7-(1-aminoethyl)-3-chloro-6-(3-fluorophenyl)-5H-thiazolo[3,2-a]pyridin-5-one (12f)

To a solution of N-(1-(3-chloro-6-(3-fluorophenyl)-5-oxo-5H-thiazolo[3,2-a]pyridin-7-yl)ethyl)-2-methylpropane-2-sulfinamide (12e) (1.65 g, 3.8 mmol) in EtOH (20 mL) was added con.HCl (5.0 mL) dropwise at r.t. and the mixture was stirred for 0.5 h. The mixture was quenched with NH$_4$OH (50 mL), extracted with DCM (2×100 mL), and the organic phase was washed with brine, dried over Na$_2$SO$_4$, and concentrated to give the crude product of 7-(1-aminoethyl)-3-chloro-6-(3-fluorophenyl)-5H-thiazolo[3,2-a]pyridin-5-one (12f), which was used for next step directly. MS-ESI (m/z): 323,325 [M+1]$^+$.

6-chloro-9-(tetrahydro-2H-pyran-2-yl)-9H-purine (12g)

6-chloro-9-(tetrahydro-2H-pyran-2-yl)-9H-purine (12g) was prepared according to the method described in WO2008153947.

3-chloro-6-(3-fluorophenyl)-7-(1-((9-(tetrahydro-2H-pyran-2-yl)-9H-purin-6-yl)amino)ethyl)-5H-thiazolo[3,2-a]pyridin-5-one (12h)

To a mixture of 6-chloro-9-(tetrahydro-2H-pyran-2-yl)-9H-purine (12g) (0.75 g, 3.1 mmol), TBAF (6 mL) and 4A Ms (0.5 g) in DMSO (6 mL) was stirred for 2 h at 30° C. under N$_2$ atmosphere, and then 7-(1-aminoethyl)-3-chloro-6-(3-fluorophenyl)-5H-thiazolo[3,2-a]pyridin-5-one (12f) (0.3 g, 1.0 mmol) was added. The mixture was stirred at r.t. for 5 h, and filtrated by cilite, diluted with 50 mL water, and extracted with EtOAc (2×50 mL). The organic phase was washed with brine (50 mL), dried over Na₂SO₄, and concentrated. The residue was purified by column chromatography on silica gel eluting with EtOAc/PE (1:1) to give 3-chloro-6-(3-fluorophenyl)-7-(1-((9-(tetrahydro-2H-pyran-2-yl)-9H-purin-6-yl)amino)ethyl)-5H-thiazolo[3,2-a]pyridin-5-one (12h). MS-ESI (m/z): 525,527 [M+1]⁺.

7-(1-((9H-purin-6-yl)amino)ethyl)-3-chloro-6-(3 fluorophenyl)-5H-thiazolo[3,2-a]pyridin-5-one (12)

To the solution of 3-chloro-6-(3-fluorophenyl)-7-(1-((9-(tetrahydro-2H-pyran-2-yl)-9H-purin-6-yl)amino)ethyl)-5H-thiazolo[3,2-a]pyridin-5-one (12h) (1.33 g, 2.5 mmol) in EtOH (15 mL)/DCM (50 mL) was added 6 N HCl (5.0 mL) at r.t., and the mixture was stirred at r.t. for 1.0 h. The mixture was quenched with NH₄OH (100 mL), extracted with DCM (2×100 mL), and the organic phase was washed with brine, dried over Na₂SO₄, and concentrated. The residue was purified by recrystallization with EtOAc to give 7-(1-((9H-purin-6-yl)amino)ethyl)-3-chloro-6-(3-fluorophenyl)-5H-thiazolo[3,2-a]pyridin-5-one (12). MS-ESI (m/z): 441, 443 [M+1]⁺.

Following essentially the same procedures described for Example 12, Example 13-19 listed in Table 2 were prepared starting from the properly substituted thioazoles and using the appropriate Grinard reagents either commercially available or readily available by methods known in the art.

TABLE 2

| EXAMPLE | STRUCTURE | NAME | DATA |
|---|---|---|---|
| 13 | 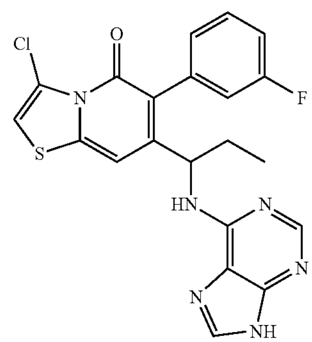 [SMILES: CCC(Nc1ncnc2[nH]cnc12)c1cc2scc(Cl)n2c(=O)c1-c1cccc(F)c1] | 7-(1-((9H-purin-6-yl)amino)propyl)-3-chloro-6-(3-fluorophenyl)-5H-thiazolo[3,2-a]pyridin-5-one | MS-ESI (m/z): 455,457 [M + 1]⁺ |
| 14 | 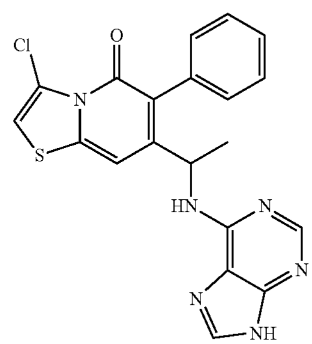 [SMILES: CC(Nc1ncnc2[nH]cnc12)c1cc2scc(Cl)n2c(=O)c1-c1ccccc1] | 7-(1-((9H-purin-6-yl)amino)ethyl)-3-chloro-6-phenyl-5H-thiazolo[3,2-a]pyridin-5-one | MS-ESI (m/z): 423,425 [M + 1]⁺ |
| 15 | 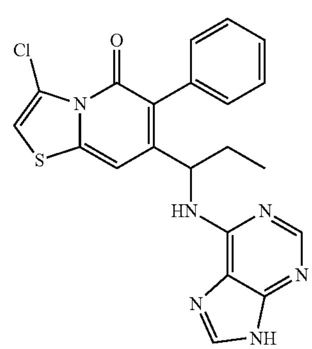 [SMILES: CCC(Nc1ncnc2[nH]cnc12)c1cc2scc(Cl)n2c(=O)c1-c1ccccc1] | 7-(1-((9H-purin-6-yl)amino)propyl)-3-chloro-6-phenyl-5H-thiazolol[3,2-a]pyridin-5-one | MS-ESI (m/z): 437,439 [M + 1]⁺ |

TABLE 2-continued

| EXAMPLE | STRUCTURE | NAME | DATA |
|---|---|---|---|
| 16 | 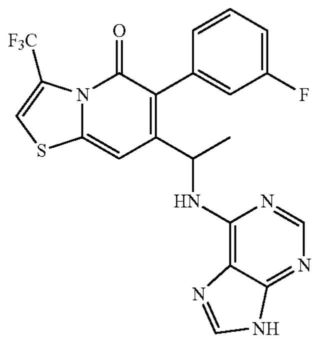 [SMILES: CC(Nc1ncnc2[nH]cnc12)c1cc2scc(C(F)(F)F)n2c(=O)c1-c1cccc(F)c1] | 7-(1-((9H-purin-6-yl)amino)ethyl)-6-(3-fluorophenyl)-3-(trifluoromethyl)-5H-thiazolo[3,2-a]pyridin-5-one | MS-ESI (m/z): 475 [M + 1]+ |
| 17 | 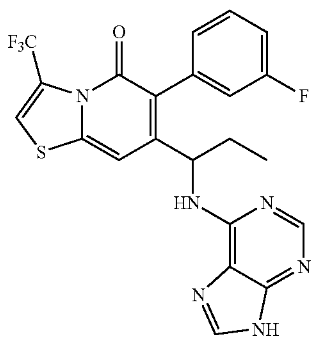 [SMILES: CCC(Nc1ncnc2[nH]cnc12)c1cc2scc(C(F)(F)F)n2c(=O)c1-c1cccc(F)c1] | 7-(1-((9H-purin-6-yl)amino)propyl)-6-(3-fluorophenyl)-3-(trifluoromethyl)-5H-thiazolo[3,2-a]pyridin-5-one | MS-ESI (m/z): 489 [M + 1]+ |
| 18 | 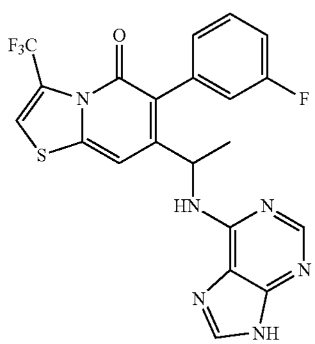 [SMILES: CC(Nc1ncnc2[nH]cnc12)c1cc2scc(C(F)(F)F)n2c(=O)c1-c1cccc(F)c1] | 7-(1-((9H-purin-6-yl)amino)ethyl)-6-phenyl-3-(trifluoromethyl)-5H-thiazol-[3,2-a]pyridin-5-one | MS-ESI (m/z): 457 [M + 1]+ |
| 19 | 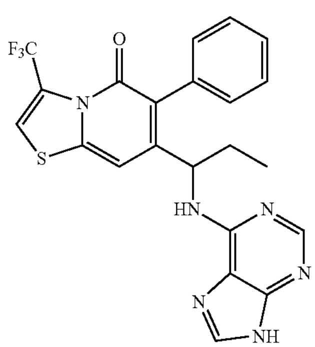 [SMILES: CCC(Nc1ncnc2[nH]cnc12)c1cc2scc(C(F)(F)F)n2c(=O)c1-c1ccccc1] | 7-(1-((9H-purin-6-yl(amino)propyl)-6-phenyl-3-(trifluoromethyl)-5H-thiazolo[3,2-a]pyridin-5-one | MS-ESI (m/z): 471 [M + 1]+ |

Example 20

7-(((9H-purin-6-yl)amino)(cyclopropyl)methyl)-3-chloro-6-(3-fluorophenyl)-5H-thiazolo[3,2-a]pyridin-5-one (20)

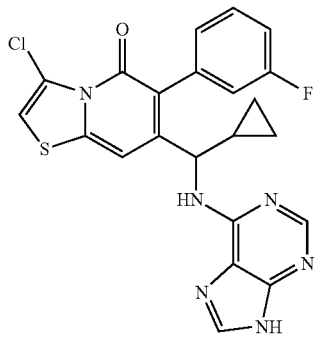

The title compound 7-(((9H-purin-6-yl)amino)(cyclopropyl)methyl)-3-chloro-6-(3-fluorophenyl)-5H-thiazolo[3,2-a]pyridin-5-one (20) was prepared according to the synthetic method of 12 by replacing (S)-tert-butansulfinamide with (R)-tert-butansulfinamide and replacing methylmagnesium bromide with cyclopropylmagnesium bromide. MS-ESI (m/z): 467,469 [M+1]$^+$.

Following essentially the same procedures described for Example 20, Example 21-23 listed in Table 3 were prepared starting from the properly substituted thioazoles and using the appropriate boronic acids either commercially available or readily available by methods known in the art.

TABLE 3

| EXAMPLE | STRUCTURE | NAME | DATA |
|---|---|---|---|
| 21 | 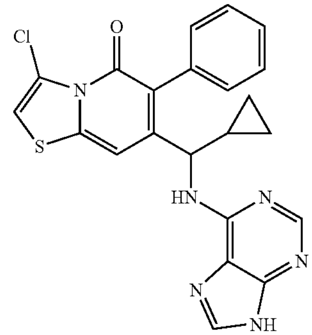 [SMILES: O=c1c(-c2ccccc2)c(C(Nc2ncnc3[nH]cnc23)C2CC2)cc2scc(Cl)n12] | 7-(((9H-purin-6-yl)amino)(cyclopropyl)methyl)-3-chloro-6-phenyl-5H-thiazolo[3,2-a]pyridin-5-one | MS-ESI (m/z): 449,451 [M + 1]$^+$ |
| 22 | 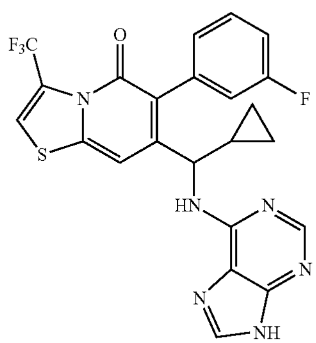 [SMILES: O=c1c(-c2cccc(F)c2)c(C(Nc2ncnc3[nH]cnc23)C2CC2)cc2scc(C(F)(F)F)n12] | 7-(((9H-purin-6-yl)amino)(cyclopropyl)methyl)-6-(3-fluorophenyl)-3-(trifluoromethyl)-5H-thiazolo[3,2-a]pyridin-5-one | MS-ESI (m/z): 501 [M + 1]$^+$ |
| 23 | 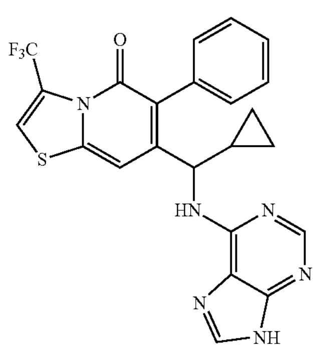 [SMILES: O=c1c(-c2ccccc2)c(C(Nc2ncnc3[nH]cnc23)C2CC2)cc2scc(C(F)(F)F)n12] | 7-(((9H-purin-6-yl)amino)(cyclopropyl)methyl)-6-phenyl-3-(trifluoromethyl)-5H-thiazolo[3,2-a]pyridin-5-one | MS-ESI (m/z): 483 [M + 1]$^+$ |

Example 24

7-(((9H-purin-6-yl)amino)(cyclopropyl)methyl)-3-methyl-6-phenyl-5H-thiazolo[3,2-a]pyridin-5-one (24)

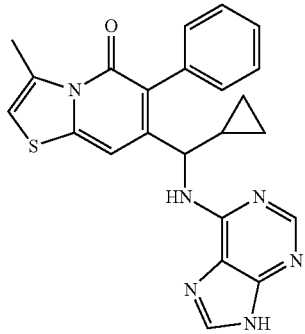

2-methyl-N-((3-methyl-5-oxo-6-phenyl-5H-thiazolo[3,2-a]pyridin-7-yl)methylene)propane-2-sulfinamide (24a)

A mixture of 3-methyl-5-oxo-6-phenyl-5H-thiazolo[3,2-a]pyridine-7-carbaldehyde (1g) (0.15 g, 0.556 mmol), (R)-tert-butansulfinamide (0.18 g, 1.488 mmol) and $Cs_2CO_3$ (0.54 g, 1.657 mol) in DCM (25 mL) was stirred at 40° C. overnight. The mixture was washed with water (25 mL), and the organic phase was washed with brine (20 mL), dried over $Na_2SO_4$ and concentrated to give the crude product of 2-methyl-N-((3-methyl-5-oxo-6-phenyl-5H-thiazolo[3,2-a]pyridin-7-yl)methylene)propane-2-sulfinamide (24a), which was used for next step directly. MS-ESI (m/z): 373 $[M+1]^+$.

N-(cyclopropyl(3-methyl-5-oxo-6-phenyl-5H-thiazolo[3,2-a]pyridin-7-yl)methyl)-2-methylpropane-2-sulfinamide (24b)

To a solution of 2-methyl-N-((3-methyl-5-oxo-6-phenyl-5H-thiazolo[3,2-a]pyridin-7-yl)methylene)propane-2-sulfinamide (24a) (0.207 g, 0.555 mmol) in THF (15 mL) was added cyclopropylmagnesiumbromide (5.0 mL, 5.0 mmol) dropwise at −78° C., and the mixture was stirred for 2 h at the same temperature. The reaction was quenched with water and the mixture was extracted with EtOAc (2×25 mL). The organic phase was washed with brine (20 mL), dried over $Na_2SO_4$, and concentrated. The residue was purified by column chromatography on silica gel eluting with EtOAc: PE (2:1) to give to N-(cyclopropyl(3-methyl-5-oxo-6-phenyl-5H-thiazolo[3,2-a]pyridin-7-yl)methyl)-2-methylpropane-2-sulfinamide (24b). MS-ESI (m/z): 415 $[M+1]^+$.

7-(amino(cyclopropyl)methyl)-3-methyl-6-phenyl-5H-thiazolo[3,2-a]pyridin-5-one (24c)

The title compound 7-(amino(cyclopropyl)methyl)-3-methyl-6-phenyl-5H-thiazolo[3,2-a]pyridin-5-one (24c) was prepared according to the synthetic method of 12f by replacing N-(1-(3-chloro-6-(3-fluorophenyl)-5-oxo-5H-thiazolo[3,2-a]pyridin-7-yl)ethyl)-2-methylpropane-2-sulfinamide (12e) with N-(cyclopropyl(3-methyl-5-oxo-6-phenyl-5H-thiazolo[3,2-a]pyridin-7-yl)methyl)-2-methylpropane-2-sulfinamide (24b). MS-ESI (m/z): 311 $[M+1]^+$.

7-(cyclopropyl((9-(tetrahydro-2H-pyran-2-yl)-9H-purin-6-yl)amino)methyl)-3-methyl-6-phenyl-5H-thiazolo[3,2-a]pyridin-5-one (24d)

A mixture of 7-(amino(cyclopropyl)methyl)-3-methyl-6-phenyl-5H-thiazolo[3,2-a]pyridin-5-one (24c) (0.062 g, 0.2 mmol), 6-chloro-9-(tetrahydro-2H-pyran-2-yl)-9H-purine (12g) (0.057 g, 0.24 mmol) and DIPEA (0.103 g, 0.8 mmol) in IPA (5 mL) was stirred at 80° C. overnight. The mixture was cooled to r.t. and the solvent was evaporated. The residue was purified by column chromatography on silica gel eluting with EtOAc to give 7-(cyclopropyl((9-(tetrahydro-2H-pyran-2-yl)-9H-purin-6-yl)amino)methyl)-3-methyl-6-phenyl-5H-thiazolo[3,2-a]pyridin-5-one (24d). MS-ESI (m/z): 513 $[M+1]^+$.

7-(((9H-purin-6-yl)amino)(cyclopropyl)methyl)-3-methyl-6-phenyl-5H-thiazolo[3,2-a]pyridin-5-one (24)

The title compound 7-(((9H-purin-6-yl)amino)(cyclopropyl)methyl)-3-methyl-6-phenyl-5H-thiazolo[3,2-a]pyridin-5-one (24) was prepared according to the synthetic method of 12 by replacing 3-chloro-6-(3-fluorophenyl)-7-(1-((9-(tetrahydro-2H-pyran-2-yl)-9H-purin-6-yl)amino)ethyl)-5H-thiazolo[3,2-a]pyridin-5-one (12h) with 7-(cyclopropyl((9-(tetrahydro-2H-pyran-2-yl)-9H-purin-6-yl)amino)methyl)-3-methyl-6-phenyl-5H-thiazolo[3,2-a]pyridin-5-one (24d) MS-ESI (m/z): 429 $[M+1]^+$.

Example 25

7-(((9H-purin-6-yl)amino)(cyclopropyl)methyl)-6-(3-fluorophenyl)-3-methyl-5H-thiazolo[3,2-a]pyridin-5-one (25)

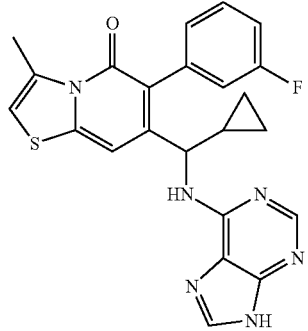

The title compound 7-(((9H-purin-6-yl)amino)(cyclopropyl)methyl)-6-(3-fluorophenyl)-3-methyl-5H-thiazolo[3,2-a]pyridin-5-one (25) was prepared according to the synthetic method of 24 by using (3-fluorophenyl)boronic acid at the Suzuki coupling step. MS-ESI (m/z): 447 $[M+1]^+$.

Example 26

2-amino-4-methyl-6-((1-(3-methyl-5-oxo-6-phenyl-5H-thiazolo[3,2-a]pyridin-7-yl)ethyl)amino)pyrimidine-5-carbonitrile (26)

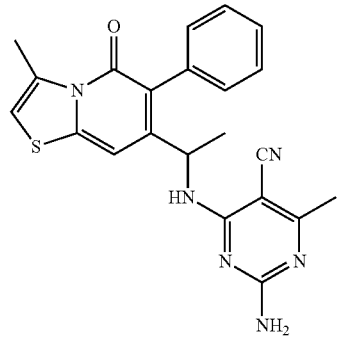

7-(1-aminoethyl)-3-methyl-6-phenyl-5H-thiazolo[3,2-a]pyridin-5-one (26a)

The title compound 7-(1-aminoethyl)-3-methyl-6-phenyl-5H-thiazolo[3,2-a]pyridin-5-one (26a) was prepared according to the synthetic method of 5g by replacing 1-(6-(4-fluorophenyl)-3-methyl-5-oxo-5H-thiazolo[3,2-a]pyridin-7-yl)ethyl methanesulfonate (5c) with 1-(3-methyl-5-oxo-6-phenyl-5H-thiazolo[3,2-a]pyridin-7-yl)ethyl methanesulfonate (1i). MS-ESI (m/z): 285 [M+1]$^+$.

2-amino-4-methyl-6-((1-(3-methyl-5-oxo-6-phenyl-5H-thiazolo[3,2-a]pyridin-7-yl)ethyl)amino)pyrimidine-5-carbonitrile (26)

The mixture of 7-(1-aminoethyl)-3-methyl-6-phenyl-5H-thiazolo[3,2-a]pyridin-5-one (26a) (0.05 g, 0.177 mmol), 2-amino-4-chloro-6-methylpyrimidine-5-carbonitrile (0.0357 g, 0.211 mmol) and DIPEA (0.0795 g, 0.62 mmol) in CH$_3$CN (1 mL) was heated at 80° C. overnight. The mixture was cooled to r.t., diluted with water (20 mL), extracted with DCM (2×20 mL). The extracts were dried over Na$_2$SO$_4$ and the solvent was evaporated. The residue was purified by recrystallization with EtOAc to give 2-amino-4-methyl-6-((1-(3-methyl-5-oxo-6-phenyl-5H-thiazolo[3,2-a]pyridin-7-yl)ethyl)amino)pyrimidine-5-carbonitrile (26). MS-ESI (m/z): 417 [M+1]$^+$.

Example 27

2-amino-4-((1-(3-chloro-6-(3-fluorophenyl)-5-oxo-5H-thiazolo[3,2-a]pyridin-7-yl)ethyl)amino)-6-methylpyrimidine-5-carbonitrile (27)

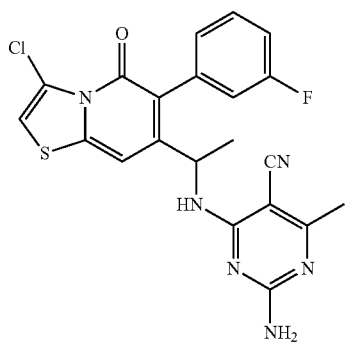

The mixture of 7-(1-aminoethyl)-3-chloro-6-(3-fluorophenyl)-5H-thiazolo[3,2-a]pyridin-5-one (12f) (0.015 g, 0.05 mmol), 2-amino-4-chloro-6-methylpyrimidine-5-carbonitrile (0.017 g, 0.1 mmol) and TEA (0.02 g, 0.2 mmol) in DMSO (1 mL) was heated at 85° C. for 1.5 h. The mixture was cooled to r.t., diluted with water (20 mL), extracted with EtOAc (2×20 mL). The extracts were dried over Na$_2$SO$_4$ and the solvent was evaporated. The residue was purified by chromatography on silica gel, eluting with EtOAc/DCM (1:2) to give 2-amino-4-((1-(3-chloro-6-(3-fluorophenyl)-5-oxo-5H-thiazolo[3,2-a]pyridin-7-yl)ethyl)amino)-6-methylpyrimidine-5-carbonitrile (27). MS-ESI (m/z): 455,457 [M+1]$^+$.

Cell Proliferation Assays

To investigate whether a compound is able to inhibit the activity of PI3K in cells, a mechanism-based assay using SU-DHL-6 cell (ATCC number: CRL 2959) was developed. In this assay, inhibition of PI3K-6 was detected by the inhibition of SUDHL-6 cells proliferation. SU-DHL-6 cells were cultured in culture flasks to 40-80% confluence in RPMI-1640 plus 10% fetal bovine serum. Cells were collected and plated onto 96-well-plates at 30000/well. Plates were incubated overnight at 37° C., with 5% CO$_2$ to adhere. Compounds were added to the plates. Final compound concentrations were 10000, 3333.3, 1111.1, 270.4, 123.5, 41.2, 13.7, 4.6 and 1.5 nM. Place plates at 37° C., with 5% CO$_2$ for 48 h. After removing the medium, 20 μl MTS/100 μl medium mixture solution were added to each well and incubate the plates for exactly 2 hours. Stop the reaction by adding 25 μl 10% SDS per well. Measure absorbance at 490 nm and 650 nm (reference wavelength). IC$_{50}$ was calculated using GraphPad Prism 5.0.

The cancer cell line WSU-NHL (DSMZ number: ACC 58) was maintained in RPMI-1640 medium with 10% FBS, at 37° C. in an atmosphere of 5% CO$_2$. The tumor cells were routinely sub-cultured twice weekly by trypsin-EDTA treatment. The cells growing in an exponential growth phase were harvested, counted, and planted in 96-well plated by 5000 cells/well. After 24 hours' culture, the series diluted test articles were added into wells, then return the assay plate into the incubator and continue culture for 48 h. At the ending point of incubation, the assay plates were detected by Promega CellTiter-Glo Luminescent Cell Viability Assay Kit (Promege 7572), and the luminescence record of each well was read by the 2104 EnVision plate reader. The data were interpreted by GraphPad Prism5 software.

Select compounds prepared as described above were assayed according to the biological procedures described herein. The results are given in the Table 5.

TABLE 5

| | IC$_{50}$ (nM) | |
|---|---|---|
| Example | SU-DHL-6 | WSU-NHL |
| 1 | 36 | / |
| 2 | 60 | / |
| 3 | 713 | / |
| 5 | 72 | / |
| 6 | 60 | / |
| 7 | 13 | / |
| 8 | 7.2 | / |
| 9 | 103 | / |
| 10 | 28 | / |
| 11 | 12 | / |
| 12 | 2.7 | 24 |
| 13 | 7.5 | 36 |
| 14 | 8.5 | 49 |

TABLE 5-continued

| Example | IC$_{50}$ (nM) | |
| --- | --- | --- |
| | SU-DHL-6 | WSU-NHL |
| 15 | 44.8 | / |
| 16 | 4.4 | 87 |
| 17 | 85 | / |
| 18 | 23 | 95 |
| 19 | 17 | / |
| 20 | 7.8 | 39 |
| 21 | 27 | 20 |
| 22 | 186 | / |
| 23 | 27 | / |
| 24 | 5.7 | 16 |
| 25 | 3.6 | 47 |
| 26 | / | <9 |
| 27 | / | <9 |

"/" denotes that it was not measured.

All references cited herein are incorporated by reference in their entirety.

What is claimed is:

1. A compound of formula (I):

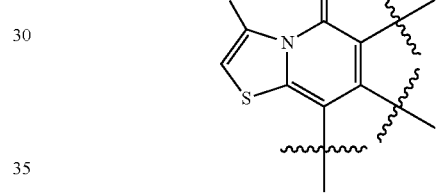

or a pharmaceutically acceptable salt thereof, wherein:
A-B is a 5-6 membered fused pyridone ring system, which is:

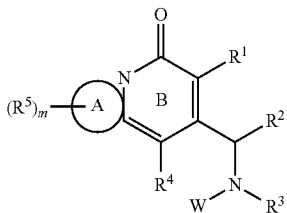

;

W is

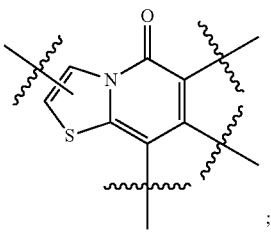

$R^1$ is selected from aryl, aryl-$C_{1-4}$ alkyl, heteroaryl, and heteroaryl-$C_{1-4}$ alkyl, wherein aryl and heteroaryl are each unsubstituted or substituted with at least one substituent independently selected from $R^{6a}$;

$R^2$ is selected from hydrogen, $C_{1-10}$ alkyl, $C_{3-10}$ cycloalkyl, $C_{3-10}$ cycloalkyl-$C_{1-4}$ alkyl, heterocyclyl, and heterocyclyl-$C_{1-4}$ alkyl, wherein alkyl, cycloalkyl, and heterocyclyl are each unsubstituted or substituted with at least one substituent independently selected from $R^{6a}$;

$R^3$ is selected from hydrogen, $C_{1-10}$ alkyl, and $C_{3-10}$ cycloalkyl, wherein alkyl and cycloalkyl are each unsubstituted or substituted with at least one substituent independently selected from $R^{6a}$;

$R^4$ is selected from hydrogen, halogen, cyano, $C_{1-10}$ alkyl, $C_{3-10}$ cycloalkyl, and $C_{3-10}$ cycloalkyl-$C_{1-4}$ alkyl, wherein alkyl and cycloalkyl are each unsubstituted or substituted with at least one substituent independently selected from $R^{6a}$;

each $R^5$ is independently selected from hydrogen, halogen, $CF_3$, $C_{1-10}$ alkyl, and $C_{3-10}$ cycloalkyl, wherein alkyl and cycloalkyl are each unsubstituted or substituted with at least one substituent independently selected from $R^{6a}$;

each $R^{6a}$ is independently selected from $C_{1-10}$ alkyl, $C_{3-10}$ cycloalkyl, $C_{3-10}$ cycloalkyl-$C_{1-4}$ alkyl, $OR^8$, $NO_2$, halogen, $SR^8$, $NR^7R^8$, and CN;

each $R^7$ and each $R^8$ are independently selected from hydrogen and $C_{1-10}$ alkyl;

m is independently selected from 0, 1, and 2.

2. The compound of claim 1 or a pharmaceutically acceptable salt thereof, wherein A-B is

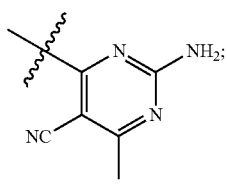 [SMILES: *c1nc(N)nc(C)c1C#N]

.

3. The compound of claim 1 or a pharmaceutically acceptable salt thereof, wherein $R^5$ is selected from hydrogen, halogen, $C_{1-6}$ alkyl, $CF_3$, and cyclopropyl.

4. The compound of claim 3 or a pharmaceutically acceptable salt thereof, wherein $R^5$ is selected from hydrogen, chloro, methyl, ethyl, $CF_3$, and cyclopropyl.

5. The compound of claim 4 or a pharmaceutically acceptable salt thereof, wherein $R^5$ is selected from chloro, methyl and $CF_3$.

6. The compound of claim 1 or a pharmaceutically acceptable salt thereof, wherein $R^1$ is aryl which is unsubstituted or substituted with at least one substituent independently selected from $R^{6a}$.

7. The compound of claim 6 or a pharmaceutically acceptable salt thereof, wherein $R^1$ is phenyl, which is unsubstituted or substituted with at least one substituent independently selected from $R^{6a}$.

8. The compound of claim 7 or a pharmaceutically acceptable salt thereof, wherein $R^1$ is phenyl, which is unsubstituted or substituted with fluoro.

9. The compound of claim 1 or a pharmaceutically acceptable salt thereof, wherein $R^2$ is selected from $C_{1-10}$ alkyl and $C_{3-10}$ cycloalkyl, wherein alkyl and cycloalkyl are unsubstituted or substituted with at least one substituent independently selected from $R^{6a}$.

10. The compound of claim 9 or a pharmaceutically acceptable salt thereof, wherein $R^2$ is selected from methyl, ethyl, isopropyl and cyclopropyl.

11. The compound of claim 1 or a pharmaceutically acceptable salt thereof, wherein $R^3$ is hydrogen.

12. The compound of claim 1 or a pharmaceutically acceptable salt thereof, wherein $R^4$ is hydrogen.

13. The compound of claim 1, selected from
2-amino-4-methyl-6-((1-(3-methyl-5-oxo-6-phenyl-5H-thiazolo[3,2-c]pyridin-7-yl)ethyl)amino)pyrimidine-5-carbonitrile,
2-amino-4-((1-(3-chloro-6-(3-fluorophenyl)-5-oxo-5H-thiazolo[3,2-c]pyridin-7-yl)ethyl)amino)-6-methylpyrimidine-5-carbonitrile,
or a pharmaceutically acceptable salt thereof.

14. A pharmaceutical composition, comprising a compound claim 1 or a pharmaceutically acceptable salt thereof, and at least one pharmaceutically acceptable carrier.

15. A compound of claim 7 or a pharmaceutically acceptable salt thereof, wherein $R^1$ is phenyl which is unsubstituted or substituted with at least one substituent independently selected from halogen.

\* \* \* \* \*

UNITED STATES PATENT AND TRADEMARK OFFICE
CERTIFICATE OF CORRECTION

PATENT NO. : 10,328,060 B2
APPLICATION NO. : 15/523315
DATED : June 25, 2019
INVENTOR(S) : Xingdong Zhao et al.

Page 1 of 1

It is certified that error appears in the above-identified patent and that said Letters Patent is hereby corrected as shown below:

In the Claims

In Column 55, Line 8, delete "[3,2-*c*]" and insert -- [3,2-*a*] --, therefor.

In Column 55, Line 13, delete "[3,2-*c*]" and insert -- [3,2-*a*] --, therefor.

Signed and Sealed this
Eighteenth Day of February, 2020

Andrei Iancu
*Director of the United States Patent and Trademark Office*